US010100069B2

(12) United States Patent
Burckhardt et al.

(10) Patent No.: US 10,100,069 B2
(45) Date of Patent: Oct. 16, 2018

(54) RAPID-CURING, MIGRATION-FREE COMPOSITION BASED ON ORGANIC POLYMERS CONTAINING SILANE GROUPS

(71) Applicant: SIKA TECHNOLOGY AG, Baar (CH)

(72) Inventors: Urs Burckhardt, Zürich (CH); Rita Cannas, Dübendorf (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/302,257

(22) PCT Filed: Apr. 16, 2015

(86) PCT No.: PCT/EP2015/058332
§ 371 (c)(1),
(2) Date: Oct. 6, 2016

(87) PCT Pub. No.: WO2014/158863
PCT Pub. Date: Oct. 22, 2015

(65) Prior Publication Data

US 2017/0037191 A1 Feb. 9, 2017

(30) Foreign Application Priority Data

Apr. 16, 2014 (EP) .................................... 14164920

(51) Int. Cl.

| | |
|---|---|
| ***B01J 31/00*** | (2006.01) |
| ***C07F 7/18*** | (2006.01) |
| ***C08G 77/26*** | (2006.01) |
| ***C08G 77/388*** | (2006.01) |
| ***C07C 279/04*** | (2006.01) |
| ***C07C 279/12*** | (2006.01) |
| ***C07C 279/16*** | (2006.01) |
| ***C07C 279/18*** | (2006.01) |
| ***C08G 65/00*** | (2006.01) |
| ***C08G 77/08*** | (2006.01) |
| ***C09D 183/08*** | (2006.01) |
| ***C09J 183/08*** | (2006.01) |

(52) U.S. Cl.
CPC ............. *C07F 7/1844* (2013.01); *B01J 31/00* (2013.01); *C07C 279/04* (2013.01); *C07C 279/12* (2013.01); *C07C 279/16* (2013.01); *C07C 279/18* (2013.01); *C07F 7/1836* (2013.01); *C08G 65/002* (2013.01); *C08G 77/08* (2013.01); *C08G 77/26* (2013.01); *C08G 77/388* (2013.01); *C09D 183/08* (2013.01); *C09J 183/08* (2013.01); *C07C 2601/14* (2017.05)

(58) Field of Classification Search
None
See application file for complete search history.

(56) References Cited

U.S. PATENT DOCUMENTS 3,984,605 A * 10/1976 Kohmura ................. C09D 5/26 427/145
4,387,150 A * 6/1983 Yabuta ..................... G03C 1/52 430/151
5,028,259 A * 7/1991 Lin
5,364,955 A 11/1994 Zwiener et al.
5,403,810 A * 4/1995 Sawamura ............. B41M 5/305 106/31.14
6,348,529 B1 * 2/2002 Yanagihara ........... C07C 279/18 524/230
9,493,691 B2 * 11/2016 Patel .................... C08G 77/455
9,732,261 B2 * 8/2017 Ireland ................... C09J 183/04
9,834,628 B2 * 12/2017 Canich .................. C08F 110/06
2003/0147845 A1 * 8/2003 Saavedra .............. C07C 291/08 424/78.26
2005/0234233 A1 * 10/2005 Ascher ................. C07D 501/00 540/225
2009/0182091 A1 * 7/2009 Noro .................... C08G 65/336 524/588
2009/0182099 A1 * 7/2009 Noro .................... C08G 65/336 525/474
2010/0004367 A1 * 1/2010 Yano .................. C08G 65/2609 524/377
2010/0063215 A1 * 3/2010 Yano .................. C08G 65/2609 525/326.5
2011/0046299 A1 2/2011 Malivemey et al.
2011/0098392 A1 4/2011 Barrandon et al.
(Continued)

FOREIGN PATENT DOCUMENTS

CN 102083912 A 6/2011
EP 1985666 A1 10/2008
(Continued)

OTHER PUBLICATIONS

Schuchardt et al. "Alkylguanidines as catalysts for the transesterification of rapeseed oil" Journal of Molecular Catalysis A: Chemical 99, 1995, 65-70.*
Aguiar et al. "Preparation of Monoglycerides by Guanidine-Catalyzed Processes" JAOCS, 75(6), 1998, 755-756.*
May 21, 2015 International Search Report issued in International Patent Application No. PCT/EP2015/058332.
Oct. 18, 2016 International Preliminary Report on Patentability issued in International Patent Application No. PCT/EP2015/058332.
(Continued)

*Primary Examiner* — Robert S Loewe
(74) *Attorney, Agent, or Firm* — Oliff PLC; Christopher W. Brown

(57) ABSTRACT

The invention relates to a composition comprising at least one organic polymer that contains silane groups and at least one catalyst of formula (I). The composition is low in emissions and low-odor, has a good shelf-life, cures rapidly to form a mechanically high-quality, durable material with a very low propensity for migration-related defects such as exudation or dirt retention by the substrate. The composition is particularly suitable for use as an adhesive, sealant or coating.

12 Claims, No Drawings

(56) References Cited

U.S. PATENT DOCUMENTS

| | | | | |
|---|---|---|---|---|
| 2011/0263743 | A1 | 10/2011 | Malivemey et al. | |
| 2011/0287268 | A1* | 11/2011 | Blanc | B01J 31/0237 428/447 |
| 2012/0172473 | A1* | 7/2012 | Maliverney | B01J 31/0251 521/134 |
| 2013/0102720 | A1* | 4/2013 | Ireland | C08L 83/04 524/400 |
| 2013/0190469 | A1 | 7/2013 | Barrandon et al. | |
| 2013/0233739 | A1* | 9/2013 | Zhao | C08K 3/34 206/223 |
| 2013/0289273 | A1* | 10/2013 | Dacko | C07D 487/04 544/279 |
| 2015/0099849 | A1* | 4/2015 | Nakamura | C08K 5/59 525/326.1 |

FOREIGN PATENT DOCUMENTS

| | | | | |
|---|---|---|---|---|
| EP | 2100923 | A1 | 9/2009 | |
| EP | 2388297 | A1 | 11/2011 | |
| FR | 2925496 | A1 | 6/2009 | |
| WO | 2009/118307 | A2 | 10/2009 | |
| WO | 2010/043353 | A1 | 4/2010 | |
| WO | WO 2013153773 | A1 * | 10/2013 | C08K 5/59 |

OTHER PUBLICATIONS

May 1, 2018 Office Action issued in Australian Patent Application No. 2015248781.

Jun. 7, 2018 Office Action issued in Chinese Patent Application No. 201580028445.3.

* cited by examiner

RAPID-CURING, MIGRATION-FREE COMPOSITION BASED ON ORGANIC POLYMERS CONTAINING SILANE GROUPS

TECHNICAL FIELD

The invention relates to compositions that are curable at room temperature and based on organic polymers containing silane groups, which are especially suitable as adhesive, sealant or coating.

STATE OF THE ART

Compositions that are curable at room temperature and are based on organic polymers containing silane groups, which are also referred to as "silane-functional polymers", "silane-modified polymers" (SMP) or "silane-terminated polymers" (STP), play a major role in many industrial applications, for example as adhesives, sealants or coatings. They are cured via crosslinking reactions of the silane groups, which are hydrolyzed under the influence of moisture, condense with one another as silanol groups and in so doing form siloxane bonds. Catalysts are frequently used to accelerate the curing. These are very often substances of toxicological concern, which constitute a potential hazard to the user and environment, especially also after curing, when the catalysts or degradation products thereof are released as a result of outgassing, migration or washing-out.

Crosslinking catalysts used conventionally are organotin compounds, especially dialkyltin(IV) carboxylates. These are notable for good activity in relation to the silanol condensation and are very hydrolysis-resistant, but they are harmful to health and a severe water pollution hazard. They are often used in combination with further catalysts, mainly basic compounds, especially amines, which specifically accelerate the preceding hydrolysis of the silane groups.

Because greater weight is being given to EHS aspects by professional organizations and users and because of stricter government regulation, there have been increased efforts for some time to exchange organotin compounds for other catalysts of lower toxicity. For instance, organotitanates, -zirconates and -aluminates have been described as alternative metal catalysts. However, these usually have lower catalytic activity in relation to the silanol condensation than the organotin compounds and bring about much slower crosslinking. Because of their lack of hydrolysis stability, they can lose a large part of their activity in the course of storage of the composition as a result of the residual moisture content of the ingredients, which causes the curing to slow significantly or stop entirely.

A further known alternative to organotin compounds is highly basic nitrogen compounds from the class of the amidines and guanidines, which can be used in combination with the metal catalysts mentioned or else alone. However, many of the commonly used amidine and guanidine catalysts, such as, in particular, 1,8-diazabicyclo[5.4.0]undec-7-ene (DBU) and 1,1,3,3-tetramethyl-guanidine (TMG), are volatile and odorous compounds that are likewise harmful to health and hazardous to the environment. Moreover, they have a tendency to migrate because of low compatibility in the composition and hence to cause separation, exudation or substrate soiling. The described use of aromatic amidines and guanidines that are solid at room temperature provides a remedy here, but requires the use of suitable solvents and brings losses in catalytic activity and hence crosslinking rate.

SUMMARY OF THE INVENTION

It is therefore an object of the present invention to provide a composition which is curable at room temperature and is based on organic polymers containing silane groups, which permits a low hazard classification, has low emission and odor levels, has good storage stability, cures rapidly by means of moisture with crosslinking of the silane groups, and at the same time forms a material of high mechanical quality and stability, which has barely any tendency to migration-related defects such as exudation and substrate soiling.

This object is achieved by a composition as claimed in claim 1, comprising a catalyst of the formula (I). These properties are also achieved without the use of metal-containing compounds as cocatalysts, especially without or with a reduced amount of organotin compounds. The catalyst of the formula (I) contains an aliphatic guanidine group and exhibits high catalytic activity, whereas aromatic guanidines are barely catalytically active, if at all.

Surprisingly, compositions of the invention have very rapid curing, attributable to the presence of the catalyst of the formula (I). The activity of the catalyst of the formula (I) is surprisingly much higher than that of comparable aliphatic guanidines, for example 1,1,3,3-tetramethylguanidine. A further surprise is the fact that compositions of the invention, neither before or after curing, have a tendency to migration-related defects such as separation, exudation or substrate soiling, in contrast to many similar compositions comprising amidine and/or guanidine catalysts according to the prior art, where catalyst-related migration effects play a major role.

A further surprise is the fact that the catalyst of the formula (I) can be prepared in the presence of the organic polymer containing silane groups, i.e. in the curable composition itself, without disruption to the system.

Further aspects of the invention are the subject of further independent claims. Particularly preferred embodiments of the invention are the subject of the dependent claims.

WAYS OF EXECUTING THE INVENTION

The present invention relates to a composition comprising at least one organic polymer containing silane groups; and at least one catalyst of the formula (I)

(I)

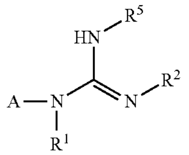

where

A is an aliphatic or cycloaliphatic or arylaliphatic hydrocarbyl radical which has 1 to 100 carbon atoms, optionally contains unsaturated moieties, optionally contains heteroatoms and optionally has amino groups or hydroxyl groups or silane groups, or together with $R^1$ is a divalent, optionally branched alkylene radical which has 4 to 12, especially 4 to 8, carbon atoms and optionally contains a heteroatom, $R^1$ is hydrogen or an alkyl or cycloalkyl or aralkyl radical having 1 to 8, especially 1 to 4, carbon atoms, or together with A is a divalent, optionally branched alkylene radical which has 4 to 12, especially 4 to 8, carbon atoms and optionally contains a heteroatom, and $R^2$ and $R^5$ are each independently an alkyl, cycloalkyl or aralkyl radical which has 1 to 18 carbon atoms and optionally contains heteroatoms;

where the catalyst of the formula (I) does not contain any nitrogen atom bonded directly to an aromatic ring or part of a heteroaromatic ring system, for example imidazole or pyrimidine.

In the present document, the term “alkoxysilane group” or “silane group” for short refers to a silyl group bonded to an organic radical and having one to three, especially two or three, hydrolyzable alkoxy radicals on the silicon atom. Correspondingly, the term “alkoxysilane” or “silane” for short refers to an organic compound having at least one silane group.

“Hydroxysilane”, “isocyanatosilane”, “aminosilane” and “mercaptosilane” refer respectively to silanes having, on the organic radical, in addition to the silane group, one or more hydroxyl, isocyanato, amino and mercapto groups.

Substance names beginning with “poly”, such as polyol or polyisocyanate, refer to substances containing, in a formal sense, two or more of the functional groups that occur in their name per molecule.

The term “organic polymer” encompasses a collective of macromolecules that are chemically homogeneous but differ in relation to degree of polymerization, molar mass and chain length, which has been prepared by a poly reaction (polymerization, polyaddition, polycondensation) and has a majority of carbon atoms in the polymer backbone, and reaction products of such a collective of macromolecules. Polymers having a polydiorganosiloxane backbone (commonly referred to as “silicones”) are not organic polymers in the context of the present document.

The term “polyether containing silane groups” also encompasses organic polymers which contain silane groups and which, in addition to polyether units, may also contain urethane groups, urea groups or thiourethane groups. Such polyethers containing silane groups may also be referred to as “polyurethanes containing silane groups”.

“Molecular weight” is understood in the present document to mean the molar mass (in grams per mole) of a molecule or part of a molecule, also referred to as “radical”. “Mean molecular weight” is understood to mean the number-average $M_n$ of an oligomeric or polymeric mixture of molecules or radicals, which is typically determined by means of gel permeation chromatography (GPC) against polystyrene as standard.

“Storage-stable” or “storable” refers to a substance or composition when it can be stored at room temperature in a suitable container over a prolonged period, typically at least 3 months up to 6 months or more, without any change in its application or use properties, especially in the viscosity and crosslinking rate, to a degree of relevance for the use thereof as a result of the storage.

A dotted line in the formulae in this document in each case represents the bond between a substituent and the corresponding molecular radical. “Room temperature” refers to a temperature of about 23° C.

The catalyst of the formula (I) may also be in tautomeric form. All possible tautomeric forms of the catalyst of the formula (I) are regarded as equivalent in the context of the present invention.

In addition, the catalyst of the formula (I) may be in protonated form.

The catalyst of the formula (I) may likewise be in complexed form, especially with cations of zinc, iron or molybdenum.

In the catalyst of the formula (I), A is especially an aliphatic or cycloaliphatic or arylaliphatic hydrocarbyl radical which has 2 to 50, preferably 3 to 30 carbon atoms, and optionally contains unsaturated moieties, optionally contains heteroatoms, especially oxygen or nitrogen atoms, and optionally has amino groups or hydroxyl groups or silane groups.

More preferably, A is selected from the group consisting of n-hexyl, n-octyl, 2-ethylhexyl, n-decyl, lauryl, cyclohexyl, benzyl, 2-methoxyethyl, 3-methoxypropyl, polyoxyalkylene radical having oxyethylene and 1,2-oxypropylene units and a molecular weight in the range from about 180 to 600 g/mol, N-methyl-3-aminopropyl, N-(2-ethylhexyl)-3-aminopropyl, N-cyclohexyl-3-aminopropyl, 3-(N,N-dimethylamino)propyl, 2-aminopropyl, 3-aminopropyl, 3-aminopentyl, 5-amino-4-methylpentyl, 5-amino-2-methylpentyl, 6-aminohexyl, 6-amino-3,3(5),5-trimethylhexyl, 6-amino-2,2(4),4-trimethylhexyl, 8-aminooctyl, 10-aminodecyl, 12-aminododecyl, 3-aminomethyl-3,5,5-trimethylcyclohexyl, 3-amino-1,5,5-trinnethylcyclohexylmethyl, 3-aminomethylcyclohexylmethyl, 4-aminomethylcyclohexylmethyl, 3-aminomethylbenzyl, 5-amino-3-oxapentyl, ω-2-aminopropylpolyoxypropylene radical having a molecular weight in the range from about 200 to 500 g/mol, 2-hydroxypropyl, 3-hydroxypropyl, 1,1-dimethyl-2-hydroxyethyl, 5-hydroxy-3-oxapentyl, 3-trimethoxysilylpropyl, 3-triethoxysilyl-propyl, 3-dimethoxymethylsilylpropyl, N-(3-trimethoxysilylpropyl)-2-aminoethyl and N-(3-triethoxysilylpropyl)-2-aminoethyl.

In one embodiment of the invention, preference is given to those A radicals that are a hydrocarbyl radical which has 6 to 30 carbon atoms and, apart from any ether oxygens, has no further functional groups, i.e. more particularly hexyl, octyl, 2-ethylhexyl, decyl, lauryl, cyclohexyl, benzyl, 2-methoxyethyl, 3-methoxypropyl or a polyoxyalkylene radical having oxyethylene and 1,2-oxypropylene units and a molecular weight in the range from about 180 to 600 g/mol. Such a catalyst of the formula (I) has zero or low moisture sensitivity and is preparable from inexpensive raw materials in a particularly simple manner and in high purity.

Surprisingly, such a catalyst free of silane groups does not migrate to the surface of the cured polymer, even though it cannot be incorporated into the organic polymer in the course of curing.

In a further preferred embodiment of the invention, preference is given to those A that are a hydrocarbyl radical which is free of silane groups and has 3 to 30 carbon atoms, optionally having ether oxygens and additionally having at least one hydroxyl group or primary or secondary amino group, i.e. more particularly N-methyl-3-aminopropyl, N-(2-ethylhexyl)-3-aminopropyl, N-cyclohexyl-3-aminopropyl, 2-aminopropyl, 3-aminopropyl, 3-aminopentyl, 5-amino-4-methylpentyl, 5-amino-2-methylpentyl, 6-aminohexyl, 6-amino-3,3(5), 5-trimethylhexyl, 6-amino-2,2(4),4-trimethylhexyl, 8-aminooctyl, 10-aminodecyl, 12-aminododecyl, 3-aminomethyl-3,5,5-trimethylcyclohexyl, 3-amino-1,5,5-trimethylcyclohexylmethyl, 3-aminomethylcyclohexylmethyl, 4-aminomethyl-cyclohexylmethyl, 3-aminomethylbenzyl, 5-amino-3-oxapentyl, ω-2-amino-propylpolyoxypropylene radical having a molecular weight in the range from 200 to 500 g/mol, 2-hydroxypropyl, 3-hydroxypropyl, 1,1-dimethyl-2-hydroxy-ethyl or 5-hydroxy-3-oxapentyl. Such a catalyst of the formula (I) has zero or low moisture sensitivity and a low odor level. Surprisingly, it is particularly nonvolatile. Because of the hydroxyl group or the primary or secondary amino group, it can have particularly high catalytic activity or particularly good interaction with the polymer containing silane groups. Surprisingly, such a catalyst free of silane groups does not migrate to the surface of the cured polymer, even though it cannot be incorporated into the organic polymer in the course of curing.

Among these, preference is given to A radicals which have a primary or secondary amino group. These catalysts of the formula (I) have particularly high catalytic activity.

In a further embodiment of the invention, preference is given to those A radicals that are a hydrocarbyl radical which is free of silane groups and has 3 to 30 carbon atoms, optionally having ether oxygen and additionally having at least one tertiary amino group, especially 3-(N,N-dimethylamino)propyl. Such a catalyst of the formula (I) has particularly high catalytic activity. Moreover, it has zero or low moisture sensitivity and a low odor level. Surprisingly, such a catalyst free of silane groups does not migrate to the surface of the cured polymer, even though it cannot be incorporated into the organic polymer in the course of curing.

In a further embodiment of the invention, preference is given to those A radicals which have a silane group, i.e. more particularly 3-trimethoxysilyl-propyl, 3-triethoxysilylpropyl, 3-dimethoxymethylsilylpropyl, N-(3-trimethoxy-silylpropyl)-2-aminoethyl or N-(3-triethoxysilylpropyl)-2-aminoethyl. Such a catalyst of the formula (I) is attached covalently in the curing of the composition, which substantially rules out migration effects.

Such a catalyst of the formula (I) containing silane groups may also be present in condensed and hence oligomeric form. In this case, two or more molecules of the formula (I) may be condensed via siloxane bonds to form linear or cyclic compounds.

Preferably, A is not the same radical as $R^2$ and $R^5$. More particularly, A is not a cyclohexyl radical when $R^2$ and $R^5$ are each a cyclohexyl radical. Catalysts of the formula (I) having the same radicals for A, $R^2$ and $R^5$ have a tendency to crystallize because of their high symmetry, which makes them difficult to process.

More preferably, $R^1$ is hydrogen. These catalysts of the formula (I) have particularly good preparability and are particularly active.

Preferably $R^2$ and $R^5$ are each independently an alkyl or cycloalkyl radical having 1 to 12, preferably 1 to 8, carbon atoms, and optionally containing heteroatoms, especially a nitrogen atom.

More preferably, $R^2$ and $R^5$ are each independently ethyl, isopropyl, tert-butyl, 3-(dimethylamino)propyl or cyclohexyl, especially isopropyl or cyclohexyl, most preferably cyclohexyl.

The preferred embodiments of the catalyst can be prepared from commercially available, inexpensive raw materials and have particularly good properties in relation to catalytic activity and compatibility of the catalyst.

Preference is given to catalysts of the formula (I) which are in liquid form at room temperature. Such catalysts are easy to convey and dose and have good incorporability into a composition, whereas solids typically require a solvent.

The weight ratio between the organic polymer containing silane groups and the catalyst of the formula (I) is preferably at least 10/1, especially at least 20/1, more preferably at least 40/1.

The weight ratio between the organic polymer containing silane groups and the catalyst of the formula (I) is preferably at most 10'000/1, especially at most 2'000/1, more preferably at most 1'000/1.

Preferably, the weight ratio between the organic polymer containing silane groups and the catalyst of the formula (I) is in the range from 10/1 to 2'000/1, more preferably 20/1 to 1'000/1, especially 40/1 to 1'000/1.

Such a composition has good storability and rapid curing.

The catalyst of the formula (I) is especially obtained by the reaction of at least one amine of the formula (II) with at least one carbodiimide of the formula (III).

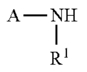

(II)

$$R^5-N=C=N-R^2$$

(III)

A, $R^1$, $R^2$ and $R^5$ have already been described above.

The reaction of the amine with the carbodiimide is preferably conducted at elevated temperature, especially at 40 to 160° C. and more preferably at 60 to 140° C. The reaction can be effected entirely without the use of VOC solvents. To accelerate the reaction, it is optionally possible to use a catalyst, especially an acid, for example a carboxylic acid or carbonic acid, or a Lewis acid, for example boron trifluoride etherate, aluminum chloride, aluminum acetylacetonate, iron(III) chloride, lithium perchlorate, zinc chloride, zinc acetate, zinc neodecanoate, zinc acetylacetonate, zinc triflate or lanthanum triflate.

The reaction can be effected in one or more stages.

The reaction is suitably effected in a substoichiometric to stoichiometric ratio in relation to the carbodiimide of the formula (III), preferably in such a ratio that 0.1 to 1.0 mol of carbodiimide of the formula (III) is used per mole of amine of the formula (II). Thus, only one amino group at most is used per amine of the formula (II), even when the amine of the formula (II) has two or more amino groups.

The reaction product from this process is preferably used in the composition without workup and/or purification, except for distillative removal of volatile compounds, optionally under reduced pressure.

The amine of the formula (II) is typically an aliphatic, cycloaliphatic or arylaliphatic amine having at least one primary or secondary amino group, especially selected from the following group:

aliphatic, cycloaliphatic or arylaliphatic monoamines optionally having ether groups, especially methylamine, ethylamine, propylamine, isopropylamine, n-butylamine, isobutylamine, sec-butylamine, tert-butylamine, n-pentyl-amine, isopentylamine, 3-methyl-2-butylamine, n-hexylamine, n-octylamine, 2-ethylhexylamine, n-decylamine, laurylamine, nnyristylamine, palmitylamine, stearylamine, cyclohexylamine, benzylamine, and fatty amines derived from natural fatty acid mixtures, for example cocoalkylamine, $C_{16}$-$C_{22}$-alkylamine, soyaalkylamine, oleylamine and tallowalkylamine, obtainable, for example, under the Armeen® (from Akzo Nobel) or Rofamin® (from Ecogreen Oleochemicals) trade names, 2-methoxyethylamine, 2-ethoxyethylamine, 2-butoxyethylamine, 2-cyclohexyloxyethylamine, 2-benzyloxyethylamine, 3-methoxypropylamine, 3-ethoxypropylamine, 3-butoxypropylamine, 3-hexyloxypropylamine, 3-(2-ethylhexyloxy)propylamine, 3-cyclohexyloxy-propylamine, 3-phenyloxypropylamine, 3-(2-methoxyethoxy)propylamine, 2(4)-methoxyphenylethylamine, morpholine, 2,6-dimethylmorpholine and 2-aminoethylmorpholine, and polyetheramines, especially polyoxyalkylene-amines, especially commercially available types such as, more particularly, Jeffamine® XTJ-581, Jeffamine® M-600, Jeffamine® M-1000, Jeffamine® M-2005, Jeffamine® M-2070 (all from Huntsman), and amines of fatty alcohol or alkylphenol alkoxylates, such as, more particularly, Jeffamine® XTJ-247, Jeffamine® XTJ-248, Jeffamine® XTJ-249, Jeffamine® XTJ-435 and Jeffamine® XTJ-436 (all from Huntsman), dimethylamine, diethylamine, dipropylamine, diisopropylamine, dibutylamine, dihexylamine, di-(2-ethylhexyl)amine, dicyclohexylamine, dibenzylamine, methylbutylamine, methylcyclohexylamine, methylbenzylamine, pyrrolidine, piperidine, 3,5-dimethylpiperidine, N-methylpiperazine and N-ethylpiperazine;

aliphatic, cycloaliphatic or arylaliphatic polyamines and hydroxylamines, especially ethylenediamine, 1,2- and 1,3-propanediamine, 2-methyl-1,2-propanediamine, 2,2-dimethyl-1,3-propanediamine, 1,3- and 1,4-butanediamine, 1,3-pentanediamine (DAMP), 1,5-pentanediamine, 1,5-diamino-2-methylpentane (MPMD), 2-butyl-2-ethyl-1,5-pentanediamine (C11 neodiamine), 1,6-hexanediamine, 2,5-dimethyl-1,6-hexanediannine, 2,2,4- and 2,4,4-trimethylhexamethylenediamine (TMD), 1,7-heptanediamine, 1,8-octanediamine, 1,9-nonanediamine, 1,10-decanediamine, 1,11-undecane-diamine, 1,12-dodecanediannine, 1,2-, 1,3- and 1,4-diaminocyclohexane, bis(4-aminocyclohexyl)methane, bis(4-amino-3-methylcyclohexyl)methane, bis(4-amino-3-ethylcyclohexyl)methane, bis(4-amino-3,5-dimethylcyclo-hexyl)methane, bis(4-amino-3-ethyl-5-methylcyclohexyl)methane, 1-amino-3-aminomethyl-3,5,5-trimethylcyclohexane (=isophoronediamine or IPD), 2- and 4-methyl-1,3-diaminocyclohexane and mixtures thereof, 1,3- and 1,4-bis(aminomethyl)cyclohexane, 2,5(2,6)-bis(aminomethyl)bicyclo[2.2.1]-heptane (NBDA), 3(4),8(9)-bis(aminomethyl)tricyclo[$5.2.1.0^{2,6}$]decane, 1,4-diamino-2,2,6-trimethylcyclohexane (TMCDA), 1,8-menthanediamine, 3,9-bis (3-aminopropyl)-2,4,8,10-tetraoxaspiro[5.5]undecane, 1,3-bis(amino-methyl) benzene, 1,4-bis(aminomethyl)benzene, N-methyl-1,2-ethane-diamine, N-ethyl-1,2-ethanediamine, N-butyl-1,2-ethanediamine, N-hexyl-1,2-ethanediamine, N-(2-ethylhexyl)-1,2-ethanediamine, N-cyclohexyl-1,2-ethanediamine, 4-aminomethylpiperidine, 3-(4-aminobutyl)piperidine, N-methyl-1,3-propanediamine, N-ethyl-1,3-propanediamine, N-butyl-1,3-propanediamine, N-hexyl-1,3-propanediamine, N-(2-ethylhexyl)-1,3-propanediamine, N-dodecyl-1,3-propanediamine, N-cyclohexyl-1,3-propane-diamine, 3-methylamino-1-pentylamine, 3-ethylamino-1-pentylamine, 3-butylamino-1-pentylamine, 3-hexylamino-1-pentylamine, 3-(2-ethylhexyl)-amino-1-pentylamine, 3-dodecylamino-1-pentylamine, 3-cyclohexylamino-1-pentylamine, N-(2-aminoethyl)piperazine, N-(2-aminopropyl)piperazine, $N^1$-((3-dimethylamino)propyl)-1,3-diaminopropane, and 3-aminopropylated fatty amines such as, more particularly, N-cocoalkyl-1,3-propanediamine, N-oleyl-1, 3-propanediamine, N-soyaalkyl-1,3-propanediamine, N-tallowalkyl-1,3-propanediamine and N—($C_{16-22}$-alkyl)-1,3-propanediamine, as obtainable, for example, under the Duomee® trade name (from Akzo Nobel), N,N-dimethyl-1, 2-ethanediamine, N,N-diethyl-1,2-ethanediamine, N,N-dimethyl-1, 3-propanediamine, N,N-diethyl-1,3-propanediamine, $N^1$,$N^1$-diethyl-1,4-pentanediamine, 2-aminoethylpiperidine, 2-aminopropylpiperidine, 2-morpholinoethylamine, 3-morpholinopropylamine, N,N'-bis(aminopropyl)-piperazine, N,N-bis(3-aminopropyl)methylamine, N,N-bis(3-aminopropyl)-ethylamine, N,N-bis(3-aminopropyl)propylamine, N,N-bis(3-aminopropyl)-cyclohexylamine, N,N-bis(3-aminopropyl)-2-ethylhexylamine, products from the double cyanoethylation and subsequent reduction of fatty amines derived from natural fatty acids, such as N,N-bis(3-aminopropyl)dodecyl-amine and N,N-bis(3-aminopropyl)tallowalkylamine, obtainable as Triameen® Y12D and Triameen® YT (from Akzo Nobel), 4-aminomethyl-1,8-octanediamine, 1,3,5-tris(aminomethyl)cyclohexane, 1,3,5-tris(amino-methyl)benzene, tris(2-aminoethyl)amine, diethylenetriannine (DETA), triethylenetetramine (TETA), tetraethylenepentamine (TEPA), penta-ethylenehexamine (PEHA), polyethylenepolya mine having 5 to 7 ethyleneamine units (called "higher ethylenepolyamine", HEPA), dipropylenetriamine (DPTA), N-(2-aminoethyl)-1,3-propanediamine (N3-amine), N,N'-bis(3-aminopropyl)ethylenediamine (N4-amine), bis-hexamethylenetriamine (BHMT), N3-(3-aminopentyl)-1,3-pentanediamine, N5-(3-aminopropyl)-2-methyl-1,5-pentanediamine and N5-(3-amino-1-ethylpropyl)-2-methyl-1,5-pentanediamine, bis(2-aminoethyl) ether, 3,6-dioxaoctane-1,8-diamine, 4,7-dioxadecane-1,10-diamine, 4,7-dioxadecane-2, 9-diamine, 4,9-dioxadodecane-1,12-diamine, 5,8-dioxadodecane-3,10-diamine, 4,7,10-trioxatridecane-1,13-diamine, cycloaliphatic diamines containing ether groups from the propoxylation and subsequent amination of 1,4-dimethylolcyclohexane, obtainable more particularly as Jeffamine® RFD-270 (from Huntsman), polyoxyalkyleneamines having a mean molecular weight in the range from 200 to 2000 g/mol, as commercially available, for example, under the Jeffamine® (from Huntsman), Polyetheramine (from BASF) and PC Amine® (from Nitroil) trade names, characterized in that they bear 2-aminopropyl or 2-aminobutyl end groups, especially Jeffamine® D-230, Jeffamine® D-400, Jeffamine® D-2000, Jeffamine® XTJ-582, Jeffamine® XTJ-578, Jeffamine® HK-511, Jeffamine® ED-600, Jeffamine® ED-900, Jeffamine® ED-2003, Jeffamine® XTJ-569, Jeffamine® XTJ-533, Jeffamine® XTJ-536, Jeffamine® THF-100, Jeffamine® THF-170, Jeffamine® THF-140, Jeffamine® THF-230, Jeffamine® SD-231, Jeffamine® SD-401, Jeffamine® SD-2001, Jeffamine® T-403, Jeffamine® XTJ-566 and Jeffamine® ST-404 (all from Huntsman), and analogous products from BASF and Nitroil, aminopropylated polyoxyalkyleneamines as obtainable by reacting polyoxyalkyleneamines with acrylonitrile and subsequent hydrogenation, polyethyleneimines, especially products commercially available under the Lupasol® (from BASF) or Epomin® (from Nippon Shokubai) brand names, such as Lupasol® FG, Lupasol® G 20 anhydrous, Epomin® SP-003, Epomin® SP-006, Epomin® SP-012 and Epomin® SP-018, 2-aminoethanol, 2-methylaminoethanol (2-amino-1-propanol), 1-amino-2-propanol, 3-amino-1-propanol, 4-amino-1-butanol, 4-amino-2-butanol, 2-amino-2-methylpropanol, 5-amino-1-pentanol, 6-amino-1-hexanol, 7-amino-1-heptanol, 8-amino-1-octanol, 10-amino-1-decanol, 12-amino-1-dodecanol, 4-(2-aminoethyl)-2-hydroxyethylbenzene, 3-aminomethyl-3,5,5-trimethylcyclohexanol; derivatives of glycols that bear a primary amino group, such as diethylene glycol, dipropylene glycol, dibutylene glycol and higher oligomers and polymers of these glycols, especially 2-(2-aminoethoxy)ethanol, 2-(2-(2-aminoethoxy)ethoxy)ethanol, alpha-(2-hydroxymethylethyl)-ω-(2-amino-methylethoxy)poly(oxy(methyl-1,2-ethanediyl)), derivatives of polyalkoxylated tri- or higher polyhydric alcohols that bear one hydroxyl group and one primary amino group, products from the single cyanoethylation and subsequent hydrogenation of glycols, especially 3-(2-hydroxyethoxy)propylamine, 3-(2-(2-hydroxyethoxy) ethoxy)propylamine and 3-(6-hydroxyhexyloxy)propylamine, aminosilanes, especially 3-aminopropyltrinnethoxysilane, 3-aminopropyl-dimethoxymethylsilane, N-(2-aminoethyl)-3-aminopropyltrimethoxysilane, N-(2-aminoethyl)-3-aminopropylmethyldimethoxysilane, N-(2-aminoethyl)-N'-[3-(trimethoxysilyl)propyl]ethylenediamine, 4-aminobutyltrimethoxysilane, 4-aminobutyldimethoxymethylsilane, 4-amino-3-methylbutyltrimethoxysilane, 4-amino-3-methylbutyldimethoxymethylsilane, 4-amino-3,3-dimethylbutyl-trimethoxysilane, 4-amino-3,3-dimethylbutyldimethoxynnethylsilane, and analogs thereof with ethoxy in place of the methoxy groups on the silicon.

Among these, preference is given to amines having at least one primary amino group.

Among these, preference is further given to amines having 2 up to 50 carbon atoms, particular preference being given to amines having 3 up to 30 carbon atoms.

Particularly preferred amines are selected from the group consisting of n-hexylamine, n-octylamine, 2-ethylhexylamine, n-decylamine, laurylamine, cyclohexylamine, benzylamine, 2-methoxyethylamine, 3-methoxypropylamine, polyoxyalkyleneamine having oxyethylene and 1,2-oxypropylene units and a mean molecular weight in the range from 180 to 600 g/mol, especially Jeffamine® M-600, N-methyl-1,3-propanediamine, N-(2-ethylhexyl)-1,3-propanediamine, N-cyclohexyl-1,3-propanediamine, N,N-dimethyl-1,3-propanediamine, 1,2-propanediamine, 1,3-propanediamine, 1,3-pentane-diamine (DAMP), 1,5-diamino-2-methylpentane (MPMD), 1,6-hexanediamine, 2,2,4- and 2,4,4-trimethylhexamethylenediamine (TMD), 1,8-octanediamine, 1,10-decanediamine, 1,12-dodecanediamine, 1-amino-3-aminomethyl-3,5,5-trimethylcyclohexane (=isophoronediamine or IPD), 1,3-bis(aminomethyl)-cyclohexane, 1,4-bis(aminomethyl)cyclohexane, 1,3-bis(aminomethyl)benzene, bis-(2-aminoethyl) ether, polyoxypropylenediamines having a mean molecular weight in the range from about 220 to 500 g/mol, especially Jeffamine® D-230 and Jeffamine® D-400, 1-amino-2-propanol, 3-amino-1-propanol, 2-amino-2-methyl-1-propanol, 2-(2-aminoethoxy)ethanol, 3-aminopropyltrimethoxysilane, 3-aminopropyltriethoxysilane, 3-aminopropyldimethoxymethylsilane, N-(2-aminoethyl)-3-aminopropyltrimethoxysilane and N-(2-aminoethyl)-3-aminopropyltriethoxysilane.

Among these, preference is given to primary monoamines lacking silane or hydroxyl groups and having 6 to 30 carbon atoms, i.e. more particularly n-hexylamine, n-octylamine, 2-ethylhexylamine, n-decylamine, laurylamine, cyclohexylamine, benzylamine, 2-methoxyethylamine, 3-methoxypropylamine and polyoxyalkyleneamine having oxyethylene and 1,2-oxypropylene units and a molecular weight in the range from 180 to 600 g/mol, especially Jeffamine® M-600. With these amines, it is possible to obtain catalysts of the formula (I) which have zero or low moisture sensitivity and are preparable from inexpensive starting materials in a particularly simple manner and in high purity.

Among these, preference is further given to hydroxylamines and polyamines that are free of silane groups and have 3 to 30 carbon atoms, especially N-methyl-1,3-propanediamine, N-(2-ethylhexyl)-1,3-propanediamine, N-cyclohexyl-1,3-propanediamine, 1,2-propanediamine, 1,3-propanediamine, 1,3-pentanediamine (DAMP), 1,5-diamino-2-methylpentane (MPMD), 1,6-hexane-diamine, 2,2(4),4-trimethylhexamethylenediamine (TMD), 1,8-octanediamine, 1,10-decanediamine, 1,12-dodecanediamine, 1-amino-3-aminomethyl-3,5,5-trimethylcyclohexane (=isophoronediamine or IPD), 1,3-bis(aminomethyl)-cyclohexane, 1,4-bis(aminomethyl) cyclohexane, 1,3-bis(aminomethyl)benzene, bis-(2-aminoethyl) ether, polyoxypropylenediamine having a molecular weight in the range from about 220 to 500 g/mol, especially Jeffamine® D-230 and Jeffamine® D-400, 1-amino-2-propanol, 3-amino-1-propanol, 2-amino-2-methyl-1-propanol and 2-(2-aminoethoxy)ethanol. With these amines, it is possible to obtain surprisingly nonvolatile catalysts of the formula (I) which have zero or low moisture sensitivity and a low odor level, and, by virtue of the hydroxyl or amino groups, can have additional effects such as a very particularly high activity or a particularly good interaction with the polymer containing silane groups.

Among these, preference is further given to polyamines that are free of silane groups, have 3 to 30 carbon atoms and have at least one tertiary amino group, especially N,N-dimethyl-1,3-propanediamine. With these amines, it is surprisingly possible to obtain active catalysts of the formula (I) having zero or low moisture sensitivity and a low odor level.

Among these, preference is given to amines containing silane groups, i.e. especially 3-aminopropyltrimethoxysilane, 3-aminopropyltriethoxysilane, 3-aminopropyldimethoxymethylsilane, N-(2-aminoethyl)-3-aminopropyltrimethoxysilane and N-(2-aminoethyl)-3-aminopropyltriethoxysilane. With these amines, it is possible to obtain catalysts of the formula (I) which are attached covalently in the course of curing of the composition, which substantially rules out migration effects.

Suitable carbodiimides are typically aliphatic, cycloaliphatic or arylaliphatic carbodiimides, especially simple, commercially available aliphatic and cycloaliphatic carbodiimides.

Preferably, the carbodiimide of the formula (III) is selected from the group consisting of N,N'-diisopropylcarbodiimide (DIC), N,N'-di-tert-butylcarbodiimide, N,N'-dicyclohexylcarbodiimide (DCC) and N-ethyl-N'-(3-dimethylamino-propyl)carbodiimide (EDC). Particular preference is given to N,N'-diisopropyl-carbodiimide (DIC) or N,N'-dicyclohexylcarbodiimide (DCC), especially DCC.

In a preferred embodiment, the catalyst of the formula (I) is prepared "in situ", i.e. in the presence of the organic polymer containing silane groups. For this purpose, the amine of the formula (II) and the carbodiimide of the formula (III) are mixed with the organic polymer containing silane groups and converted at a temperature in the range from 40 to 120° C. The in situ reaction can especially also be conducted in the presence of further ingredients as typical of curable compositions based on organic polymers containing silane groups, especially in the presence of auxiliaries and additives as described further down. Surprisingly, the reaction to give the catalyst of the formula (I) can also be effected in situ in a fully formulated sealant or adhesive or coating, each based on an organic polymer containing silane groups, i.e. also in the presence of, for example, desiccants and/or plasticizers and/or fillers and/or rheology modifiers. The in situ preparation of the catalyst of the formula (I) in the composition is particularly preferred, since the catalyst thus only forms with a certain time delay and hence disrupts the compounding process to a small degree. This can constitute a significant advantage in practice, for example in the case of moist constituents such as fillers, which can thus be dried in the composition when desiccants, and the moisture content of which thus does not react with involvement of the catalyst with silane groups of the organic polymer containing silane groups. As a result, the viscosity of the composition is not increased in an unwanted manner.

Particularly preferred catalysts of the formula (I) are selected from the group consisting of 1-hexyl-2,3-diisopropylguanidine, 1-hexyl-2,3-dicyclohexyl-guanidine, 1-octyl-2,3-diisopropylguanidine, 1-octyl-2,3-dicyclohexylguanidine, 1-(2-ethylhexyl)-2,3-diisopropylguanidine, 1-(2-ethylhexyl)-2,3-dicyclohexyl-guanidine, 1-decyl-2,3-diisopropylguanidine, 1-decyl-2,3-dicyclohexyl-guanidine, 1-lauryl-2,3-diisopropylguanidine, 1-lauryl-2,3-dicyclohexyl-guanidine, 1-cyclohexyl-2,3-diisopropylguanidine, 1,2,3-tricyclohexylguanidine, 1-benzyl-2,3-diisopropylguanidine, 1-benzyl-2,3-dicyclohexylguanidine, 1-(2-methoxyethyl)-2,3-diisopropylguanidine, 1-(2-methoxyethyl)-2,3-dicyclohexyl-guanidine, 1-(2-methoxypropyl)-2,3-diisopropylguanidine, 1-(2-methoxypropyl)-2,3-dicyclohexylguanidine, 1-(ω-methoxy-polyoxypropylene-polyoxyethylene)-2, 3-diisopropylguanidine with a molecular weight in the range from about 320 to 750 g/mol, 1-(ω-methoxy-polyoxypropylene-polyoxyethylene)-2,3-dicyclohexylguanidine with a molecular weight in the range from about 400 to 830 g/mol, 1-(2-aminopropyl)-2,3-diisopropylguanidine, 1-(2-aminopropyl)-2, 3-dicyclohexylguanidine, 1-(3-aminopropyl)-2,3-diisopropylguanidine, 1-(3-amino-propyl)-2,3-dicyclohexylguanidine, 1-(3-methylaminopropyl)-2, 3-diisopropyl-guanidine, 1-(3-nnethylaminopropyl)-2,3-dicyclohexylguanidine, 1-(3-(2-ethylhexylamino)propyl)-2,3-diisopropylguanidine, 1-(3-(2-ethylhexylamino)propyl)-2, 3-dicyclohexylguanidine, 1-(3-cyclohexylaminopropyl)-2,3-diisopropyl-guanidine, 1-(3-cyclohexylaminopropyl)-2,3-dicyclohexylguanidine, 1-(3-(N, N-dimethylamino)propyl)-2,3-diisopropylguanidine, 1-(3-(N,N-dimethylamino)-propyl)-2, 3-dicyclohexylguanidine, 1-(3-aminopentyl)-2,3-diisopropylguanidine, 1-(3-aminopentyl)-2,3-dicyclohexylguanidine, 1-(5-amino-4-methylpentyl)-2, 3-diisopropylguanidine, 1-(5-amino-4-methylpentyl)-2,3-dicyclohexylguanidine, 1-(5-amino-2-methylpentyl)-2,3-diisopropylguanidine, 1-(5-amino-2-methyl-pentyl)-2, 3-dicyclohexylguanidine, 1-(6-aminohexyl)-2,3-diisopropylguanidine, 1-(6-aminohexyl)-2,3-dicyclohexylguanidine, 1-(6-amino-2,2(4),4-trimethylhexyl)-2,3-diisopropylguanidine, 1-(6-amino-2,2(4),4-trimethylhexyl)-2, 3-dicyclohexylguanidine, 1-(6-amino-3,3(5),5-trimethylhexyl)-2, 3-diisopropyl-guanidine, 1-(6-amino-3,3(5),5-trimethylhexyl)-2,3-dicyclohexylguanidine, 1-(8-aminooctyl)-2,3-diisopropylguanidine, 1-(8-aminooctyl)-2,3-dicyclohexyl-guanidine, 1-(10-aminodecyl)-2,3-diisopropylguanidine, 1-(10-aminodecyl)-2, 3-dicyclohexylguanidine, 1-(12-aminododecyl)-2,3-diisopropylguanidine, 1-(12-aminododecyl)-2, 3-dicyclohexylguanidine, 1-(3-aminomethyl-3,5,5-trimethyl-cyclohexyl)-2, 3-diisopropylguanidine, 1-(3-aminomethyl-3,5,5-trimethylcyclo-hexyl)-2,3-dicyclohexylguanidine, 1-(3-amino-1,5,5-trimethylcyclohexylmethyl)-2, 3-diisopropylguanidine, 1-(3-amino-1,5,5-trimethylcyclohexylmethyl)-2,3-dicyclohexylguanidine, 1-(3-aminomethylcyclohexylmethyl)-2,3-diisopropyl-guanidine, 1-(3-aminomethylcyclohexylmethyl)-2,3-dicyclohexylguanidine, 1-(4-aminomethylcyclohexylmethyl)-2, 3-diisopropylguanidine, 1-(4-aminomethyl-cyclohexylmethyl)-2,3-dicyclohexylguanidine, 1-(3-aminomethylbenzyl)-2,3-diisopropylguanidine, 1-(3-aminomethylbenzyl)-2,3-dicyclohexylguanidine, 1-(5-amino-3-oxapentyl)-2,3-diisopropylguanidine, 1-(5-amino-3-oxapentyl)-2, 3-dicyclohexylguanidine, 1-(ω-2-aminopropylpolyoxypropylene)-2,3-diisopropyl-guanidine with a molecular weight in the range from about 340 to 650 g/mol, 1-((aminopolyoxypropylene)yl)-2,3-dicyclohexylguanidine with a molecular weight in the range from about 420 to 750 g/mol, 1-(2-hydroxypropyl)-2,3-diisopropylguanidine, 1-(2-hydroxypropyl)-2,3-dicyclohexylguanidine, 1-(3-hydroxypropyl)-2, 3-diisopropylguanidine, 1-(3-hydroxypropyl)-2,3-dicyclohexylguanidine, 1-(2-hydroxy-1, 1-dimethylethyl)-2,3-diisopropylguanidine, 1-(2-hydroxy-1, 1-dimethylethyl)-2, 3-dicyclohexylguanidine, 1-(5-hydroxy-3-oxapentyl)-2,3-diisopropylguanidine, 1-(5-hydroxy-3-oxapentyl)-2,3-dicyclohexylguanidine, 1-(3-trimethoxysilylpropyl)-2,3-diisopropylguanidine, 1-(3-trimethoxysilylpropyl)-2, 3-dicyclohexylguanidine, 1-(3-triethoxysilylpropyl)-2,3-diisopropylguanidine, 1-(3-triethoxysilylpropyl)-2,3-dicyclohexylguanidine, 1-(3-dimethoxymethyl-silylpropyl)-2, 3-diisopropylguanidine, 1-(3-diniethoxymethylsilylpropyl)-2, 3-dicyclohexylguanidine, 1-(N-(3-trimethoxysilylpropyl)-2-aminoethyl)-2, 3-diisopropylguanidine, 1-(N-(3-trimethoxysilylpropyl)-2-aminoethyl)-2, 3-dicyclohexylguanidine, 1-(N-(3-triethoxysilylpropyl)-2-aminoethyl)-2, 3-diisopropylguanidine and 1-(N-(3-triethoxysilylpropyl)-2-aminoethyl)-2, 3-dicyclohexylguanidine.

Among these, preference is given to guanidine with no silane groups, no amino groups and no hydroxyl groups. These guanidines have zero or low moisture sensitivity and can be prepared in particularly pure form.

Among these, preference is further given to guanidines having primary or secondary amino groups or hydroxyl groups and having no silane groups. These guanidines are surprisingly nonvolatile and have zero or low moisture sensitivity and a low odor level and, as a result of the hydroxyl or amino groups, can have additional effects such as a very particularly high activity or a particularly good interaction with the polymer containing silane groups.

Among these, preference is further given to guanidines having tertiary amino groups and having no silane groups. These guanidines have surprisingly high catalytic activity and zero or low moisture sensitivity and have a low odor level. Among these, preference is further given to guanidines containing silane groups. These guanidines are covalently attached in the course of curing of the composition, which substantially rules out migration effects.

The organic polymer containing silane groups is preferably a polyolefin, polyester, polyamide, poly(meth)acrylate or polyether or a mixed form of these polymers, each of which bears one or preferably more silane groups. The silane groups may be in lateral chain positions or in terminal positions and are bonded to the organic polymer via a carbon atom.

More preferably, the organic polymer containing silane groups is a polyolefin containing silane groups or a polyester containing silane groups or a poly(meth)acrylate containing silane groups or a polyether containing silane groups or a mixed form of these polymers. Most preferred is a polyether containing silane groups.

Preferred silane groups on the organic polymer are end groups of the formula (IV)

(IV)

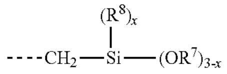

where $R^7$ is a linear or branched, monovalent hydrocarbyl radical having 1 to 5 carbon atoms, especially methyl or ethyl or isopropyl;

$R^8$ is a linear or branched, monovalent hydrocarbyl radical having 1 to 8 carbon atoms, especially methyl or ethyl; and x is a value of 0 or 1 or 2, preferably 0 or 1, especially 0.

More preferably $R^7$ is methyl or ethyl.

For particular applications, the $R^7$ radical is preferably an ethyl group, since, in this case, ecologically and toxicologically harmless ethanol is released in the course of curing of the composition.

Particular preference is given to trimethoxysilane groups, dimethoxymethylsilane groups or triethoxysilane groups.

In this context, methoxysilane groups have the advantage that they are particularly reactive, and ethoxysilane groups have the advantage that they are toxicologically advantageous and particularly storage-stable.

The organic polymer containing silane groups has an average of preferably 1.3 to 4, especially 1.5 to 3, more preferably 1.7 to 2.8, silane groups per molecule.

The silane groups are preferably terminal.

The organic polymer containing silane groups preferably has a mean molecular weight, determined by means of GPC against a polystyrene standard, in the range from 1000 to 30'000 g/mol, especially from 2000 to 20'000 g/mol. The organic polymer containing silane groups preferably has a silane equivalent weight of 300 to 25'000 g/eq, especially of 500 to 15'000 g/eq.

The organic polymer containing silane groups may be solid or liquid at room temperature. It is preferably liquid at room temperature.

Most preferably, the organic polymer containing silane groups is a polymer containing silane groups which is liquid at room temperature, where the silane groups are especially dialkoxysilane groups and/or trialkoxysilane groups, more preferably trimethoxysilane groups or triethoxysilane groups.

Processes for preparing polyethers containing silane groups are known to the person skilled in the art.

In one process, polyethers containing silane groups are obtainable from the reaction of polyethers containing allyl groups with hydrosilanes, optionally with chain extension using, for example, diisocyanates.

In a further process, polyethers containing silane groups are obtainable from the copolymerization of alkylene oxides and epoxysilanes, optionally with chain extension using, for example, diisocyanates.

In a further process, polyethers containing silane groups are obtainable from the reaction of polyether polyols with isocyanatosilanes, optionally with chain extension using diisocyanates.

In a further process, polyethers containing silane groups are obtainable from the reaction of polyethers containing isocyanate groups, especially NCO-terminated urethane polyethers from the reaction of polyether polyols with a superstoichiometric amount of polyisocyanates, with aminosilanes, hydroxysilanes or mercaptosilanes. Polyethers containing silane groups from this process are particularly preferred. This process enables the use of a multitude of inexpensive starting materials of good commercial availability, by means of which it is possible to obtain different polymer properties, for example high extensibility, high strength, low modulus of elasticity, low glass transition point or high weathering resistance.

More preferably, the polyether containing silane groups is obtainable from the reaction of NCO-terminated urethane polyethers with aminosilanes or hydroxysilanes. Suitable NCO-terminated urethane polyethers are obtainable from the reaction of polyether polyols, especially polyoxyalkylenediols or polyoxyalkylenetriols, preferably polyoxypropylenediols or polyoxypropylenetriols, with a superstoichiometric amount of polyisocyanates, especially diisocyanates.

Preferably, the reaction between the polyisocyanate and the polyetherpolyol is conducted with exclusion of moisture at a temperature of 50° C. to 160° C., optionally in the presence of suitable catalysts, with metered addition of the polyisocyanate in such a way that the isocyanate groups thereof are present in a stoichiometric excess in relation to the hydroxyl groups of the polyol. More particularly, the excess of polyisocyanate is chosen such that a content of free isocyanate groups of 0.1% to 5% by weight, preferably 0.2% to 4% by weight, more preferably 0.3% to 3% by weight, based on the overall polymer, remains in the resulting urethane polyether after the reaction of all hydroxyl groups.

Preferred diisocyanates are selected from the group consisting of 1, 6-hexamethylene diisocyanate (HDI), 1-isocyanato-3,3, 5-trimethyl-5-isocyanatomethylcyclohexane (=isophorone diisocyanate or IPDI), 2,4- and 2,6-tolylene diisocyanate and any desired mixtures of these isomers (TDI) and 4,4'-, 2,4'- and 2,2'-diphenylmethane diisocyanate and any desired mixtures of these isomers (MDI). Particular preference is given to IPDI or TDI. Most preferred is IPDI. In this way, polyethers containing silane groups with particularly good lightfastness are obtained.

Especially suitable as polyether polyols are polyoxyalkylenediols or polyoxyalkylenetriols having a degree of unsaturation lower than 0.02 meq/g, especially lower than 0.01 meq/g, and a mean molecular weight in the range from 400 to 25'000 g/mol, especially 1000 to 20'000 g/mol.

As well as polyether polyols, it is also possible to use portions of other polyols, especially polyacrylate polyols, and low molecular weight diols or triols.

Suitable aminosilanes for the reaction with an NCO-terminated urethane polyether are primary and secondary aminosilanes. Preference is given to 3-aminopropyltrimethoxysilane, 3-aminopropyldimethoxymethylsilane, 4-aminobutyltrimethoxysilane, 4-amino-3-methylbutyltrimethoxysilane, 4-amino-3,3-dimethylbutyltrimethoxysilane, N-butyl-3-aminopropyltrimethoxysilane, N-phenyl-3-aminopropyltrimethoxysilane, adducts formed from primary amino-silanes such as 3-aminopropyltrimethoxysilane, 3-aminopropyldimethoxy-methylsilane or N-(2-aminoethyl)-3-aminopropyltrimethoxysilane and Michael acceptors such as acrylonitrile, (meth)acrylic esters, (meth)acrylamides, maleic or fumaric diesters, citraconic diesters or itaconic diesters, especially dimethyl or diethyl N-(3-trimethoxysilylpropyl)aminosuccinate. Likewise suitable are analogs of the aminosilanes mentioned with ethoxy or isopropoxy groups in place of the methoxy groups on the silicon.

Suitable hydroxysilanes for the reaction with an NCO-terminated urethane polyether are especially obtainable from the addition of aminosilanes onto lactones or onto cyclic carbonates or onto lactides.

Aminosilanes suitable for the purpose are especially 3-aminopropyltrimeth-oxysilane, 3-aminopropyltriethoxysilane, 4-aminobutyltrinnethoxysilane, 4-aminobutyltriethoxysilane, 4-amino-3-methylbutyltrimethoxysilane, 4-amino-3-methylbutyltriethoxysilane, 4-amino-3,3-dimethylbutyltrimethoxysilane, 4-amino-3,3-dimethylbutyltriethoxysilane, 2-aminoethyltrimethoxysilane or 2-aminoethyltriethoxysilane. Particular preference is given to 3-aminopropyltrimethoxysilane, 3-aminopropyltriethoxysilane, 4-amino-3,3-dimethylbutyl-trimethoxysilane or 4-amino-3,3-dimethylbutyltriethoxysilane.

Suitable lactones are especially γ-valerolactone, γ-octalactone, δ-decalactone, and ε-decalactone, especially γ-valerolactone.

Suitable cyclic carbonates are especially 4,5-dimethyl-1,3-dioxolan-2-one, 4,4-dimethyl-1,3-dioxolan-2-one, 4-ethyl-1,3-dioxolan-2-one, 4-methyl-1, 3-dioxolan-2-one or 4-(phenoxymethyl)-1,3-dioxolan-2-one.

Suitable lactides are especially 1,4-dioxane-2,5-dione (lactide formed from 2-hydroxyacetic acid, also called "glycolide"), 3,6-dimethyl-1,4-dioxane-2,5-dione (lactide formed from lactic acid, also called "lactide") and 3,6-diphenyl-1, 4-dioxane-2,5-dione (lactide formed from mandelic acid).

Preferred hydroxysilanes which are obtained in this way are N-(3-triethoxysilylpropyl)-2-hydroxypropanamide, N-(3-trimethoxysilylpropyl)-2-hydroxypropanamide, N-(3-triethoxysilylpropyl)-4-hydroxypentanamide, N-(3-triethoxysilylpropyl)-4-hydroxyoctanamide, N-(3-triethoxysilylpropyl)-5-hydroxydecanamide and N-(3-triethoxysilylpropyl)-2-hydroxypropyl carbamate.

In addition, suitable hydroxysilanes are also obtainable from the addition of aminosilanes onto epoxides or from the addition of amines onto epoxysilanes. Preferred hydroxysilanes which are obtained in this way are 2-morpholino-4(5)-(2-trimethoxysilylethyl)cyclohexan-1-ol, 2-morpholino-4(5)-(2-triethoxysilyl-ethyl) cyclohexan-1-ol or 1-morpholino-3-(3-(triethoxysilyl)propoxy)propan-2-ol.

Further suitable polyethers containing silane groups are commercially available products, especially the following: MS Polymer™ (from Kaneka Corp.; especially the S203H, S303H, S227, S810, MA903 and S943 products); MS Polymer™ or Silyl™ (from Kaneka Corp.; especially the SAT010, SAT030, SAT200, 5AX350, SAX400, SAX725, MAX450, MAX951 products); Excestar® (from Asahi Glass Co. Ltd.; especially the S2410, S2420, S3430, S3630 products); SPUR+* (from Momentive Performance Materials; especially the 1010LM, 1015LM, 1050MM products); Vorasil™ (from Dow Chemical Co.; especially the 602 and 604 products); Desmoseal® (from Bayer MaterialScience AG; especially the S XP 2458, S XP 2636, S XP 2749, S XP 2774 and S XP 2821 products), TEGOPAC® (from Evonik Industries AG; especially the Seal 100, Bond 150, Bond 250 products), Polymer ST (from Hanse Chemie AG/Evonik Industries AG, especially the 47, 48, 61, 61LV, 77, 80, 81 products); Geniosil® STP (from Wacker Chemie AG; especially the E10, E15, E30, E35 products).

Particularly preferred end groups of the formula (IV) are end groups of the formula (V),

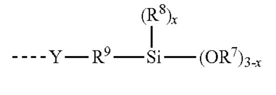

(V)

where $R^9$ is a linear or branched divalent hydrocarbyl radical which has 1 to 12 carbon atoms and optionally has cyclic and/or aromatic moieties and optionally one or more heteroatoms, especially one or more nitrogen atoms;

Y is a divalent radical selected from —O—, —S—, —N($R^{10}$)—, —O—CO—N($R^{10}$)—, —N($R^{10}$)—CO—O— and —N($R^{10}$)—CO—N($R^{10}$)—, where $R^{19}$ is hydrogen or a linear or branched hydrocarbyl radical which has 1 to 20 carbon atoms and optionally has cyclic moieties, and which optionally has an alkoxysilyl, ether or carboxylic ester group; and $R^7$, $R^8$ and x have the definitions already given above.

Preferably, $R^9$ is 1,3-propylene or 1,4-butylene, where butylene may be substituted by one or two methyl groups.

More preferably, $R^9$ is 1,3-propylene.

In addition to the catalyst of the formula (I), the composition of the invention may contain further catalysts for the crosslinking of the silane groups. Suitable further catalysts are especially metal catalysts and/or basic nitrogen or phosphorus compounds.

Possible metal catalysts are especially compounds of tin, titanium, zirconium, aluminum or zinc, especially diorganotin(IV) compounds such as, in particular, dibutyltin(IV) diacetate, dibutyltin(IV) dilaurate, dibutyltin(IV) dineodecanoate or dibutyltin(IV) bis(acetylacetonate) and dioctyltin (IV) dilaurate, and also titanium(IV) or zirconium(IV) or aluminum(III) or zinc(II) complexes, especially with alkoxy, carboxylate, 1,3-diketonate, 1,3-ketoesterate or 1,3-ketoamidate ligands.

Possible basic nitrogen or phosphorus compounds are especially imidazoles, pyridines, phosphazene bases or preferably amines, hexahydrotriazines, biguanides, amidines or guanidines which do not correspond to the formula (I).

Suitable amines are especially alkyl-, cycloalkyl- or aralkylamines such as triethylamine, triisopropylamine, 1-butylamine, 2-butylamine, tert-butylamine, 3-methyl-1-butylamine, 3-methyl-2-butylamine, dibutylamine, tributylamine, hexylamine, dihexylamine, cyclohexylamine, dicyclohexylamine, dimethylcyclohexylamine, benzylamine, dibenzylamine, dimethylbenzylamine, octylamine, 2-ethylhexylamine, di-(2-ethylhexyl)amine, laurylamine, N,N-dimethyllaurylamine, stearylamine, N,N-dimethylstearylamine; fatty amines derived from natural fatty acid mixtures, such as, more particularly, cocoalkylamine, N,N-dimethylcocoalkylamine, $C_{16-22}$-alkylamine, N,N-dimethyl-C16-22-alkylamine, soyaalkylamine, N,N-dimethylsoyaalkylamine, oleylamine, N,N-dimethyloleylamine, tallowalkylamine or N,N-dimethyltallowalkylamine, obtainable, for example, under the Armeen® (from Akzo Nobel) or Rofamin® (from Ecogreen Oleochemicals) trade names; aliphatic, cycloaliphatic or araliphatic diamines such as ethylenediamine, butanediamine, hexamethylenediamine, dodecanediamine, neopentanediamine, 2-methyl-pentamethylenediamine (MPMD), 2,2(4),4-trimethylhexannethylenediamine (TMD), isophoronediamine (IPD), 2,5(2,6)-bis-(aminomethyl)bicyclo[2.2.1]-heptane (NBDA), 1,3-xylylenediamine (MXDA), N,N'-di(tert-butyl)ethylenediamine, N,N,N',N'-tetramethylethylenediamine, N,N,N',N'-tetramethyl-propylenediamine, N,N,N',N'-tetramethylhexamethylenediamine, 3-dimethylaminopropylamine, 3-(methylamino)propylamine, 3-(cyclohexylamino)-propylamine, piperazine, N-methylpiperazine, N,N'-dimethylpiperazine, 1, 4-diazabicyclo[2.2.2]octane, fatty polyamines such as N-cocoalkyl-1,3-propane-diamine, N-oleyl-1,3-propanediamine, N-soyaalkyl-1,3-propanediamine, N-tallowalkyl-1,3-propanediamine or N—($C_{16-22}$-alkyl)-1,3-propanediamine, obtainable, for example, under the Duomeen® trade name (from Akzo Nobel); polyalkyleneamines such as diethylenetriamine, dipropylenetriamine, triethylenetetramine (TETA), tetraethylenepentamine (TEPA), pentamethylenehexamine (PEHA), 3-(2-aminoethyl)aminopropylamine, N,N'-bis(3-amino-propyl) ethylenediamine, N-(3-aminopropyl)-N-methylpropanediamine, bis(3-dimethylaminopropyl) amine, N-(3-dimethylaminopropyl)-1,3-propylenediamine, N-(2-aminoethyl)piperazine (N-AEP), N-(2-aminopropyl) piperazine, N,N'-di-(2-aminoethyl)piperazine, 1-methyl-4-(2-dimethylaminoethyl)piperazine, N,N,N',N",N"-pentamethyldiethylenetriamine, N,N,N',N",N"-pentamethyldipropylenetriamine, polyethyleneimines, obtainable, for example, under the Lupasol® (from BASF) and Epomin® (from Nippon Shokubai) trade names; etheramines such as, more particularly, 2-methoxyethylamine, 2-ethoxyethylamine, 3-methoxypropylamine, 3-ethoxypropylamine, 3-(2-ethylhexyloxy)propylamine, 3-(2-methoxyethoxy)propylamine, 2(4)-methoxyphenylethylamine, morpholine, N-methylmorpholine, N-ethyl-morpholine, 2-aminoethylmorpholine, bis(2-aminoethyl) ether, bis(dimethyl-aminoethyl) ether, bis(dimorpholinoethyl) ether, N,N,N'-trimethyl-N'-hydroxyethylbis (2-aminoethyl) ether, 3,6-dioxaoctane-1,8-diamine, 4, 7-dioxadecane-1,10-diamine, 4,7-dioxadecane-2,9-diamine, 4,9-dioxadodecane-1, 12-diamine, 5,8-dioxadodecane-3,10-diamine, 4,7,10-trioxatridecane-1, 13-diamin or 2-aminopropyl-terminated glycols as obtainable, for example, under the Jeffamine® trade name (from Huntsman); amino alcohols such as, more particularly, ethanolamine, isopropanolamine, diethanolamine, diisopropanolamine, triethanolamine, triisopropanolamine, N-butylethanolamine, diglycolamine, N,N-diethylethanolamine, N-methyldiethanolamine, N-methyldiisopropylamine, N,N,N'-trimethylaminoethylethanolamine, N-(3-dimethylaminopropyl)-N, N-diisopropanolamine, N,N-bis(3-dimethylaminopropyl)-N-isopropanolamine, 2-(2-dimethylaminoethoxy)ethanolamine or adducts formed from mono- and polyamines with epoxides or diepoxides; amines containing phenol groups, such as, more particularly, condensation products formed from phenols, aldehydes and amines (what are called Mannich bases and phenalkamines), such as, more particularly, 2-(dimethylaminomethyl)phenol, 2,4, 6-tris(dimethyl-aminomethyl)phenol or polymers formed from phenol, formaldehyde and N,N-dimethyl-1,3-propanediamine, and also phenalkamines commercially available under the Cardolite® (from Cardolite), Aradur® (from Huntsman) and Beckopox® (from Cytec) brand names; polyamines containing amide groups, called polyamidoamines, as commercially available, for example, under the Versamid® (from Cognis), Aradur® (from Huntsman), Euretek® (from Huntsman) or Beckopox® (from Cytec) brand names; or aminosilanes such as, more particularly 3-aminopropyltrimethoxysilane, 3-aminopropyldimethoxy-methylsilane, N-(2-aminoethyl)-3-aminopropyltrimethoxysilane, N-(2-aminoethyl)-3-aminopropylmethyldimethoxysilane, N-(2-aminoethyl)-N'-[3-(trimethoxysilyl)propyl]ethylenediamine or analogs thereof with ethoxy in place of the methoxy groups on the silicon.

Suitable triazines are especially 1,3,5-hexahydrotriazine or 1,3,5-tris (3-(dimethylamino)propyl)hexahydrotriazine.

Suitable biguanides are especially biguanide, 1-butylbiguanide, 1,1-dimethylbiguanide, 1-butylbiguanide, 1-phenylbiguanide or 1-(o-tolyl)biguanide (OTBG).

Suitable amidines are especially 1,8-diazabicyclo[5.4.0]undec-7-ene (DBU), 1,5-diazabicyclo[4.3.0]non-5-ene (DBN), 6-dibutylamino-1, 8-diazabicyclo-[5.4.0]undec-7-ene, 6-dibutylamino-1,8-diazabicyclo[5.4.0]undec-7-ene, N,N'-di-n-hexylacetamidine (DHA), 2-methyl-1,4,5,6-tetrahydropyrimidine, 1, 2-dimethyl-1,4,5,6-tetrahydropyrinnidine, 2,5,5-trimethyl-1,4,5, 6-tetrahydro-pyrimidine, N-(3-trimethoxysilylpropyl)-4,5-dihydroimidazole or N-(3-triethoxy-silylpropyl)-4,5-dihydroimidazole.

Suitable guanidines which do not correspond to the formula (I) are especially 1-butylguanidine, 1,1-dimethylguanidine, 1,3-dimethylguanidine, 1,1,3,3-tetra-methylguanidine (TMG), 2-(3-(trimethoxysilyl)propyl)-1,1,3,3-tetramethylguanidine, 2-(3-(methyldimethoxysilyl)propyl)-1,1,3,3-tetramethylguanidine, 2-(3-(triethoxysilyl)propyl)-1,1,3,3-tetramethylguanidine, 1,5, 7-triazabicyclo-[4.4.0]dec-5-ene (TBD), 7-methyl-1,5,7-triazabicyclo[4.4.0]dec-5-ene, 7-cyclohexyl-1,5,7-triazabicyclo[4.4.0]dec-5-ene, 1-phenylguanidine, 1-(o-tolyl)guanidine (OTG), 1,3-diphenylguanidine, 1,3-di(o-tolyl)guanidine or 2-guanidinobenzimidazole.

In addition, the composition of the invention may comprise, as cocatalyst, an acid, especially a carboxylic acid. Preference is given to aliphatic carboxylic acids such as formic acid, lauric acid, stearic acid, isostearic acid, oleic acid, 2-ethyl-2,5-dimethylcaproic acid, 2-ethylhexanoic acid, neodecanoic acid, fatty acid mixtures from the hydrolysis of natural fats and oils or di- and polycarboxylic acids, especially poly(meth)acrylic acids.

In a preferred embodiment, the composition of the invention is essentially free of organotin compounds. Organotin-free compositions are advantageous in terms of protection of health and protection of the environment. More particularly, the tin content of the composition is less than 0.1% by weight, especially less than 0.05% by weight.

In a further preferred embodiment, the composition of the invention comprises a combination of at least one catalyst of the formula (I) and at least one organotin compound, especially a diorganotin(IV) compound such as those mentioned above. Such a composition already has a high curing rate coupled with a low tin content, which is advantageous for toxicological and environmental reasons. The tin content of the composition is especially less than 1% by weight.

In one embodiment of the invention, the composition additionally comprises, as well as the organic polymer containing silane groups and a catalyst of the formula (I), at least one organotitanate. A combination of catalyst of the formula (I) and organotitanate has particularly high catalytic activity. This enables rapid curing of the composition with a comparatively small use amount of the catalyst of the formula (I).

Suitable organotitanates are especially titanium(IV) complexes.

Preferred organotitanates are especially selected from

- titanium(IV) complexes having two 1,3-diketonate ligands, especially 2, 4-pentanedionate (=acetylacetonate), and two alkoxide ligands;
- titanium(IV) complexes having two 1,3-ketoesterate ligands, especially ethylacetoacetate, and two alkoxide ligands;
- titanium(IV) complexes having one or more aminoalkoxide ligands, especially triethanolamine or 2-((2-aminoethyl)amino)ethanol, and one or more alkoxide ligands;
- titanium(IV) complexes having four alkoxide ligands;
- and more highly condensed organotitanates, especially oligomeric titanium(IV) tetrabutoxide, also referred to as polybutyl titanate;

where suitable alkoxide ligands are especially isobutoxy, n-butoxy, isopropoxy, ethoxy and 2-ethylhexoxy.

Especially suitable are the commercially available products Tyzor® AA, GBA, GBO, AA-75, AA-65, AA-105, DC, BEAT, BTP, TE, TnBT, KTM, TOT, TPT or IBAY (all from Dorf Ketal); Tytan PBT, TET, X85, TAA, ET, S2, S4 or S6 (all from Borica Company Ltd.) and Ken-React® KR® TTS, 7, 9QS, 12, 26S, 33DS, 38S, 39DS, 44, 134S, 138S, 133DS, 158FS or LICA® 44 (all from Kenrich Petrochemicals).

Very particularly suitable organotitanates are selected from bis(ethylacetoacetato)diisobutoxytitanium(IV) (commercially available, for example, as Tyzor® IBAY from Dorf Ketal), bis(ethylacetoacetato)diisopropoxytitanium (IV) (commercially available, for example, as Tyzor® DC from Dorf Ketal), bis(acetylacetonato)diisopropoxytitanium (IV), bis(acetylacetonato)diisobutoxytitanium(IV), tris(oxyethyl)amine-isopropoxy-titanium(IV), bis[tris(oxyethyl)amin]diisopropoxytitanium(IV), bis(2-ethylhexane-1, 3-dioxy) titanium(IV), tris[2-((2-aminoethyl)amino)ethoxy] ethoxytitanium(IV), bis(neopentyl(diallyl)oxy) diethoxytitanium(IV), titanium(IV) tetrabutoxide, tetra(2-ethylhexyloxy) titanate, tetra(isopropoxy) titanate and polybutyl titanate.

Most preferred are bis(ethylacetoacetato)diisobutoxytitanium(IV) or bis(ethylacetoacetato)diisopropoxytitanium (IV).

In an organotitanate-containing composition, the weight ratio between the organic polymer containing silane groups and the catalyst of the formula (I) is preferably in the range from 40/1 to 2'000/1.

The weight ratio between the organotitanate and the catalyst of the formula (I) is preferably in the range from 10/1 to 1/10, more preferably 5/1 to 1/5, especially 5/1 to 1/3.

The composition of the invention may comprise further constituents, especially the following auxiliaries and additives:

- adhesion promoters and/or crosslinkers, especially aminosilanes such as, in particular, 3-aminopropyltrimethoxysilane, 3-aminopropyldimethoxymethyl-silane, N-(2-aminoethyl)-3-aminopropyltrimethoxysilane, N-(2-aminoethyl)-3-aminopropyldimethoxymethylsilane, N-(2-aminoethyl)-N'-[3-(trimethoxysilyl)-propyl] ethylenediannine or the analogs thereof with ethoxy in place of methoxy groups, and also N-phenyl-, N-cyclohexyl- or N-alkylaminosilanes, mercaptosilanes, epoxysilanes, (meth)acryloylsilanes, anhydridosilanes, carbamatosilanes, alkylsilanes or iminosilanes, oligomeric forms of these silanes, adducts formed from primary aminosilanes with epoxysilanes or (meth)acryloylsilanes or anhydridosilanes. Especially suitable are 3-amino-propyltrimethoxysilane, 3-aminopropyltriethoxysilane, N-(2-aminoethyl)-3-aminopropyltrimethoxysilane, N-(2-aminoethyl)-3-aminopropyltriethoxy-silane, 3-glycidoxypropyltrimethoxysilane, 3-glycidoxypropyltriethoxysilane or 3-ureidopropyltrimethoxysilane, or oligomeric forms of these silanes;
- desiccants, especially tetraethoxysilane, vinyltrimethoxysilane, vinyltriethoxysilane or organoalkoxysilanes having a functional group in the α position to the silane group, especially N-(methyldimethoxysilylmethyl)-O-methylcarbamate, (methacryloyloxymethypsilanes, methoxymethylsilanes, orthoformic esters, calcium oxide or molecular sieves, especially vinyltrimethoxysilane or vinyltriethoxysilane;
- plasticizers, especially carboxylic esters such as phthalates, especially dioctyl phthalate, bis(2-ethylhexyl) phthalate, bis(3-propylheptyl) phthalate, diisononyl phthalate or diisodecyl phthalate, diesters of ortho-cyclohexane-dicarboxylic acid, especially diisononyl 1,2-cyclohexanedicarboxylate, adipates, especially dioctyl adipate, bis(2-ethylhexyl) adipate, azelates, especially bis(2-ethylhexyl) azelate, sebacates, especially bis(2-ethylhexyl) sebacate or diisononyl sebacate, polyols, especially polyoxyalkylene polyols or polyester polyols, glycol ethers, glycol esters, organic phosphoric or sulfonic esters, sulfonamides, polybutenes, or fatty acid methyl or ethyl esters derived from natural fats or oils, also called "biodiesel";
- solvents;
- inorganic or organic fillers, especially natural, ground or precipitated calcium carbonates, optionally coated with fatty acids, especially stearic acid, baryte (heavy spar), talcs, quartz flours, quartz sand, dolomites, wollastonites, kaolins, calcined kaolins, mica (potassium aluminum silicate), molecular sieves, aluminum oxides, aluminum hydroxides, magnesium hydroxide, silicas including finely divided silicas from pyrolysis processes, industrially produced carbon blacks, graphite, metal powders such as aluminum, copper, iron, silver or steel, PVC powder or hollow spheres;
- fibers, especially glass fibers, carbon fibers, metal fibers, ceramic fibers or polymer fibers such as polyamide fibers or polyethylene fibers;
- dyes;
- pigments, especially titanium oxide or iron oxides;
- rheology modifiers, especially thickeners, especially sheet silicates such as bentonites, derivatives of castor oil, hydrogenated castor oil, polyamides, polyurethanes, urea compounds, fumed silicas, cellulose ethers or hydrophobically modified polyoxyethylenes;
- stabilizers against oxidation, heat, light and UV radiation;
- natural resins, fats or oils such as rosin, shellac, linseed oil, castor oil or soya oil;
- non-reactive polymers such as, in particular, homo- or copolymers of unsaturated monomers, especially from the group comprising ethylene, propylene, butylene, isobutylene, isoprene, vinyl acetate or alkyl (meth) acrylates, especially polyethylenes (PE), polypropylenes (PP), polyisobutylenes, ethylene-vinyl acetate copolymers (EVA) or atactic poly-α-olefins (APAO);
- flame-retardant substances, especially the already mentioned fillers aluminum hydroxide and magnesium hydroxide, or, in particular, organic phosphoric esters such as, in particular, triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenyl phosphate), bisphenol A bis (diphenyl phosphate) or ammonium polyphosphates;
- surface-active substances, especially wetting agents, leveling agents, deaerating agents or defoamers;
- biocides, especially algicides, fungicides or substances that inhibit fungal growth;

and other substances customarily used in moisture-curing compositions. It may be advisable to chemically or physically dry certain constituents before mixing them into the composition.

In a preferred embodiment, the composition comprises at least one desiccant and at least one adhesion promoter and/or crosslinker.

In a preferred embodiment, the composition does not comprise any phthalates as plasticizers. Such compositions are toxicologically advantageous and have fewer problems with migration effects.

The composition of the invention is preferably produced and stored with exclusion of moisture. Typically, the composition is storage-stable with exclusion of moisture in a suitable package or arrangement, such as, more particularly, a bottle, a canister, a pouch, a bucket, a vat or a cartridge.

The composition of the invention may take the form of a one-component or of a multi-component, especially two-component, composition. The composition of the invention is preferably a one-component composition.

In the present document, "one-component" refers to a composition in which all constituents of the composition are stored in a mixture in the same container and which is curable with moisture.

In the present document, "two-component" refers to a composition in which the constituents of the composition are present in two different components which are stored in separate containers. Only shortly before or during the application of the composition are the two components mixed with one another, whereupon the mixed composition cures, and the curing proceeds or is completed only via the action of moisture.

The composition of the invention is especially applied within a temperature range between 5 and 45° C., preferably at ambient temperature, and also cures under these conditions.

On application of the composition described to at least one solid body or article, the silane groups present in the composition come into contact with moisture. On contact with moisture, the silane groups are hydrolyzed. This forms silanol groups (Si—OH groups), and subsequent condensation reactions form siloxane groups (Si—O—Si groups). Any further moisture-reactive groups present likewise react with moisture present. As a result of these reactions, the composition cures. The catalyst of the formula (I) accelerates this curing. The water required for the curing may either originate from air (air humidity), or else the above-described composition can be contacted with a water-containing component, for example by painting, for example with a smoothing agent, or by spraying, or it is possible to add water or a water-containing component to the composition in the course of application, for example in the form of an aqueous or water-releasing liquid or paste. A paste is especially suitable if the composition itself is in the form of a paste. It is especially mixed in by means of a static mixer or by means of a dynamic mixer. Such a water-containing component is added to the composition of the invention typically in a weight ratio of composition of the invention to water-containing component in the range from 5:1 to 200:1, preferably 10:1 to 100:1, especially 10:1 to 50:1. In the case of curing by means of air humidity, the composition cures from the outside inward, with initial formation of a skin at the surface of the composition. What is called the skin time is a measure of the curing rate of the composition. The rate of curing is generally determined by various factors, for example the availability of water, the temperature, etc.

The composition of the invention has good storability, permits a low hazard classification on account of the low toxicity and low volatility of the catalyst of the formula (I), and enables low-emissions and low-odor compositions which cure rapidly and in so doing form a durable material of high mechanical quality. It is a particularly advantageous circumstance that this material has barely any tendency to migration-related defects such as exudation or substrate soiling, by contrast with compositions comprising catalysts according to the prior art, for example DBU, TMG, DHA or titanium(IV) complexes. Compositions comprising such catalysts have a tendency to migration effects after curing, which can be manifested by tacky and/or greasy surfaces and/or by substrate soiling after curing. Such effects are extremely undesirable, since tacky and greasy surfaces are rapidly soiled and are difficult to paint over, and substrate contamination can lead to lasting discoloration.

The composition of the invention is suitable for a multitude of uses, especially as a paint, lacquer or primer, as a resin for production of fiber composites, as a potting compound, sealant, adhesive, covering, coating or paint for construction and industrial applications, for example as a seam seal, cavity seal, electrical insulation compound, spackling compound, joint sealant, weld or crimp seam sealant, assembly adhesive, bodywork adhesive, glazing adhesive, sandwich element adhesive, laminating adhesive, laminate adhesive, packaging adhesive, wood adhesive, parquet adhesive, anchoring adhesive, floor covering, floor coating, balcony coating, roof coating, concrete protection coating, parking garage coating, seal, pipe coating, anticorrosion coating, textile coating, primer, damping element, sealing element or spackling compound.

In the application, the composition of the invention is applied to at least one substrate.

Suitable substrates are especially

- glass, glass ceramic, concrete, mortar, brick, tile, gypsum and natural rocks such as limestone, granite or marble;
- metals and alloys such as aluminum, iron, steel and nonferrous metals, and also surface-finished metals and alloys such as galvanized or chromed metals;
- leather, textiles, paper, wood, woodbase materials bonded with resins, for example phenolic, melamine or epoxy resins, resin-textile composites and further polymer composites;
- plastics such as polyvinyl chloride (rigid and flexible PVC), acrylonitrile-butadiene-styrene copolymers (ABS), polycarbonate (PC), polyamide (PA), polyesters, poly(methyl methacrylate) (PMMA), epoxy resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), and also fiber-reinforced plastics such as carbon fiber-reinforced plastics (CFP), glass fiber-reinforced plastics (GFP) and sheet molding compounds (SMC), where the plastics may preferably have been surface-treated by means of plasma, corona or flames;
- coated substrates such as powder-coated metals or alloys;
- paints and lacquers, especially automotive topcoats.

If required, the substrates can be pretreated prior to the application of the composition, especially by chemical and/or physical cleaning methods or by the application of an adhesion promoter, an adhesion promoter solution or a primer.

The composition of the invention is particularly suitable for contact with substrates that are particularly sensitive to defects caused by migrating substances, especially by the formation of discoloration or specks. These are, in particular, fine-pore substrates such as marble, limestone or other natural stones, gypsum, cement mortar or concrete, but also plastics. Especially on PVC, severe discoloration is observed in the presence of catalysts, for example DBU or TMG, and cannot be removed by cleaning. No such effects are observed with the catalysts of the formula (I).

The composition is particularly suitable as an adhesive and/or sealant, especially for joint sealing and for elastic adhesive bonds in construction and industrial applications, and as elastic coating with crack-bridging properties, especially for protection and/or sealing of, for example, roofs, floors, balconies, parking decks or concrete pipes.

More particularly, the present invention thus also relates to the use of an above-described composition as adhesive, sealant or coating. Such a composition typically comprises plasticizers, fillers, adhesion promoters and/or crosslinkers and desiccants and optionally further auxiliaries and additives.

Typically, the content of organic polymer containing silane groups in the composition of the invention is 10% to 80% by weight, especially 15% to 60% by weight, preferably 15% to 50% by weight, based on the total weight of the composition.

For an application as an adhesive or sealant, the composition preferably has a pasty consistency with structurally viscous properties. Such a pasty sealant or adhesive is especially applied to a substrate from standard cartridges which are operated manually, by means of compressed air or with a battery, or from a vat or hobbock by means of a delivery pump or an extruder, optionally by means of an application robot.

For an application as a coating, the composition preferably has a liquid consistency at room temperature with self-leveling properties. It may be slightly thixotropic, such that the coating is applicable to sloping to vertical surfaces without flowing away immediately. It is especially applied by means of a roller or brush or by pouring-out and distribution by means, for example, of a roller, a scraper or a notched trowel.

It is possible to bond or seal two identical or two different substrates, especially the aforementioned substrates.

The invention further relates to a cured composition obtainable from a composition as described above, after curing thereof with water, especially in the form of air humidity.

It is a feature of the cured composition that it has barely any tendency, if any at all, to migration-related defects such as exudation or substrate soiling. This is in contrast with cured compositions based on organic polymers containing silane groups and containing amidine or guanidine catalysts, as known from the prior art, where catalyst-related migration effects are known, as already mentioned.

The use as an adhesive, sealant or coating gives rise to an article which has been bonded, sealed or coated with a composition of the invention. The article is especially a built structure, especially a structure built by structural engineering or civil engineering, an industrially manufactured good or a consumable good, especially a window, a domestic appliance or a mode of transport such as, more particularly, an automobile, a bus, a truck, a rail vehicle, a ship, an aircraft or a helicopter; or the article may be an installable component thereof.

The present invention further relates to the use of a catalyst of the formula (I) as described above as crosslinking catalyst for curable compositions, especially for curable compositions containing silane groups, especially for compositions as described above.

In a preferred use of the catalyst of the formula (I), the moisture-curing composition is essentially free of organotin compounds. More particularly, the tin content of the composition is less than 0.06% by weight, especially less than 0.01% by weight.

The present invention further provides a catalyst of the formula (I a)

(Ia)

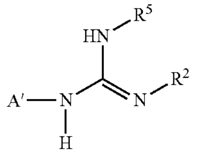

where

A' is an aliphatic or cycloaliphatic or arylaliphatic hydrocarbyl radical which has 6 to 30 carbon atoms and optionally contains ether oxygens, and which does not have any silane groups, any hydroxyl groups or any amino groups, and and $R^2$ and $R^5$ have the definitions already described.

A catalyst of the formula (I a) has zero or low moisture sensitivity, has a low odor level and is preparable in high purity in a simple process.

It is particularly suitable as catalyst for the formation of siloxane groups. More particularly, it is suitable as crosslinking catalyst for polymers containing silane groups such as, more particularly, polyorganosiloxanes having terminal silane groups or organic polymers containing silane groups as described above.

Surprisingly, in spite of the absence of silane groups, it does not migrate to the surface of such a cured polymer, even though it cannot be incorporated into the polymer in the course of curing.

The present invention further provides a catalyst of the formula (I b)

(Ib)

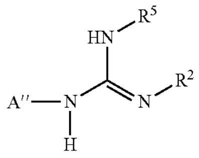

where

A" is an aliphatic or cycloaliphatic or arylaliphatic hydrocarbyl radical which has 3 to 30 carbon atoms and is free of silane groups, optionally contains ether oxygens and has at least one hydroxyl group or primary or secondary amino group, and $R^2$ and $R^5$ have the definitions already described.

A catalyst of the formula (I b) has zero or low moisture sensitivity and a low odor level. It is particularly nonvolatile and surprisingly has particularly good compatibility with polymers containing silane groups. Because of the hydroxyl group or the primary or secondary amino group, it can possess particularly high catalytic activity or have particularly good interaction with a polymer containing silane groups. Surprisingly, in spite of the absence of silane groups, it does not migrate to the surface of such a cured polymer, even though it cannot be incorporated into a polymer containing silane groups in the course of curing. Such a catalyst is also suitable for formation of further guanidine-functional compounds.

A catalyst of the formula (I b) is particularly suitable as a catalyst for the formation of siloxane groups.

It is especially suitable as a crosslinking catalyst for polymers containing silane groups such as, more particularly, polyorganosiloxanes having terminal silane groups or organic polymers containing silane groups.

The present invention further provides a catalyst of the formula (I c)

(Ic)

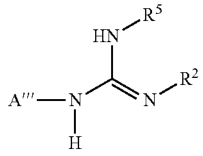

where

A'' is an aliphatic or cycloaliphatic or arylaliphatic hydrocarbyl radical which has 3 to 30 carbon atoms, is free of silane groups, optionally contains ether oxygen and has at least one tertiary amino group, and $R^2$ and $R^5$ have the definitions already described.

A catalyst of the formula (I c) has zero or low moisture sensitivity and a low odor level. It surprisingly possesses very particularly high catalytic activity for acceleration of curing of polymers containing silane groups and has very good compatibility therein. Surprisingly, in spite of the absence of silane groups, it does not migrate to the surface of such a cured polymer, even though it cannot be incorporated into the polymer in the course of curing.

A catalyst of the formula (I c) is particularly suitable as catalyst for the formation of siloxane groups.

More particularly, it is suitable as crosslinking catalyst for polymers containing silane groups such as, more particularly, polyorganosiloxanes having terminal silane groups or organic polymers containing silane groups.

Suitable organic polymers containing silane groups have already been described above.

A suitable polyorganosiloxane having terminal silane groups especially has the formula (VI)

(VI)

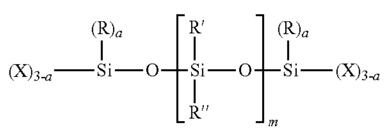

where

R, R' and R'' are each independently a monovalent hydrocarbyl radical having 1 to 12 carbon atoms;

X is a hydroxyl radical or an alkoxy, acetoxy, ketoximato, amido or eneoxy radical having 1 to 13 carbon atoms;

a is 0, 1 or 2; and m is an integer in the range from 50 to about 2,500.

R is preferably methyl, vinyl or phenyl.

R' and R'' are preferably each independently an alkyl radical having 1 to 5, preferably 1 to 3 carbon atoms, especially methyl.

X is preferably a hydroxyl radical or an alkoxy or ketoximato radical having 1 to 6 carbon atoms, especially a hydroxyl, methoxy, ethoxy, methylethylketoximato or methylisobutylketoximato radical.

More preferably, X is a hydroxyl radical.

a is preferably 0 or 1, especially 0.

In addition, m is preferably chosen such that the polyorganosiloxane of the formula (VI) at room temperature has a viscosity in the range from 100 to 500'000 mPa·s, especially from 1000 to 100'000 mPa·s.

Such polyorganosiloxanes are easy to handle and crosslink with moisture and/or silane crosslinkers to give solid silicone polymers having elastic properties.

Suitable commercially available polyorganosiloxanes are available, for example, from Wacker, Momentive Performance Materials, GE Advanced Materials, Dow Corning, Bayer or Shin Etsu.

The polyorganosiloxane having terminal silane groups may comprise a silane crosslinker, especially a silane of the formula (VII)

$$(R''')_q\text{—Si—}(X')_{4-q} \qquad \text{(VII)}$$

where

R''' is a monovalent hydrocarbyl radical having 1 to 12 carbon atoms,

X' is a hydroxyl radical or an alkoxy, acetoxy, ketoximato, amido or eneoxy radical having 1 to 13 carbon atoms; and q has a value of 0, 1 or 2, especially 0 or 1.

Particularly suitable silanes of the formula (VII) are methyltrimethoxysilane, ethyltrimethoxysilane, propyltrimethoxysilane, vinyltrimethoxysilane, methyltriethoxysilane, vinyltriethoxysilane, phenyltriethoxysilane, tetramethoxysilane, tetraethoxysilane, methyltris(methylethylketoximo)silane, vinyltris(methylethylketoximo)silane and methyltris(isobutylketoximo)silane.

EXAMPLES

Adduced hereinafter are working examples which are intended to elucidate the invention described in detail. It will be appreciated that the invention is not restricted to these described working examples.

"Standard climatic conditions" refer to a temperature of 23±1° C. and a relative air humidity of 50±5%.

$^1H$ NMR spectra were measured on a spectrometer of the Bruker Ascend 400 type at 400.14 MHz; the chemical shifts δ are reported in ppm relative to tetramethylsilane (TMS). No distinction was made between true and pseudo-coupling patterns.

Infrared spectra (FT-IR) were measured on a Nicolet iS5 FT-IR instrument from Thermo Scientific equipped with a horizontal ATR measurement unit with a diamond crystal. Liquid samples were applied undiluted as films; solid samples were dissolved in $CH_2Cl_2$. The absorption bands are reported in wavenumbers ($cm^{-1}$) (measurement window: 4000-650 $cm^{-1}$).

Viscosities were measured on a thermostated Rheotec RC30 cone-plate viscometer (cone diameter 50 mm, cone angle 1°, cone tip-plate distance 0.05 mm, shear rate 10 $s^{-1}$).

The skin time (ST) was determined by applying a few grams of the composition to cardboard in a layer thickness of about 2 mm and measuring, under standard climatic conditions, the time until, when the surface of the composition was gently tapped by means of an LOPE pipette, no residues remained any longer on the pipette for the first time. The characteristics of the surface were tested by touch.

The mechanical properties of tensile strength, elongation at break and modulus of elasticity (at 0-5% and at 0-50% elongation) were measured in accordance with DIN EN 53504 at a pulling speed of 200 win/min.

Preparation of Catalysts of the Formula (I)

Catalyst K-1: 1-(3-Triethoxysilylpropyl)-2,3-dicyclohexylguanidine

In a round-bottom flask, 6.69 g of 3-aminopropyltriethoxysilane and 5.17 g of N,N'-dicyclohexylcarbodiimide were mixed and the mixture was heated to 100° C. while stirring. At regular intervals, the reaction mixture was examined by means of FT-IR spectroscopy. After 40 hours, the carbodiimide band at about 2120 $cm^{-1}$ had disappeared completely. Thereafter, the reaction mixture was freed of the volatile constituents under reduced pressure. This gave 11.38 g of a colorless, low-odor oil.

$^1$H NMR ($CDCl_3$): δ0.5-0.75 (m, 2H, $CH_2Si$), 1.1-1.4 (m, 21H), 1.55-2.0 (m, 10H), 2.95-3.1 (m, 2H, $NCH^{Cy}$), 3.1-3.3 (m, 2H, $CH_2N$), 3.85 (q, 6H, $CH_2O$). FT-IR: 2972, 2924, 2851, 1641 (C═N), 1496, 1447, 1389, 1363, 1326, 1297, 1237, 1165, 1101, 1074, 953, 888, 773.

Catalyst K-2: 1-(3-Trimethoxysilylpropyl)-2,3-dicyclohexylguanidine

In a round-bottom flask, 6.42 g of 3-aminopropyltrimethoxysilane and 5.73 g of N,N'-dicyclohexylcarbodiimide were mixed and the mixture was heated to 110° C. while stirring. At regular intervals, the reaction mixture was examined by means of FT-IR spectroscopy. After 24 hours, the carbodiimide band at about 2120 $cm^{-1}$ had disappeared completely. Thereafter, the reaction mixture was freed of the volatile constituents under reduced pressure. This gave 10.66 g of a pale yellow, low-odor oil.

$^1$H NMR ($CDCl_3$): δ0.5-0.75 (m, 2H, $CH_2Si$), 1.1-1.4 (m, 12H), 1.55-2.0 (m, 10H), 2.95-3.1 (m, 2H, $NCH^{Cy}$), 3.1-3.3 (m, 2H, $CH_2N$), 3.55 (s, 9H, $CH_3O$).

FT-IR: 3405 (N—H), 2923, 2849, 1639 (C═N), 1498, 1448, 1327, 1305, 1237, 1189, 1081, 979, 889, 814, 787, 713.

Catalyst K-3: 1-(N-(3-Trimethoxysilylpropyl)-2-aminoethyl)-2,3-dicyclohexyl-guanidine In a round-bottom flask, 6.11 g of N-(2-aminoethyl)-3-aminopropyltrimethoxy-silane (Silquest® A-1120, from Momentive) and 5.16 g of N,N'-dicyclohexyl-carbodiimide were mixed and the mixture was heated to 120° C. while stirring. At regular intervals, the reaction mixture was examined by means of FT-IR spectroscopy. After 25 hours, the carbodiimide band at about 2120 $cm^{-1}$ had disappeared completely. This gave a colorless, low-odor oil.

$^1$H NMR ($CDCl_3$): δ0.6-0.7 (m, 2H, $CH_2Si$), 1.0-1.5 (m, 10H), 1.55-2.0 (m, 12H), 2.60 (m, 2H, $CH_2N$), 2.75 (m, 2H, $CH_2N$), 2.9 (m, 1H, $NCH^{Cy}$), 3.11 (m, 2H, $CH_2N$), 3.23 (m, 1H, $NCH^{Cy}$), 3.5-3.6 (br s, 9H, $CH_3O$).

FT-IR: 3233, 2924, 2839, 1637 (C═N), 1605, 1538, 1448, 1409, 1364, 1330, 1269, 1257, 1189, 1079, 889, 813, 781.

Catalyst K-4: 1-(N-(3-Triethoxysilylpropyl)-2-aminoethyl)-2, 3-dicyclohexyl-guanidine In a round-bottom flask, 7.27 g of N-(2-aminoethyl)-3-aminopropyltriethoxy-silane (Geniosil® GF-94, from Wacker Chemie) and 5.16 g of N, N'-dicyclohexylcarbodiimide were mixed and the mixture was heated to 120° C. while stirring. At regular intervals, the reaction mixture was examined by means of FT-IR spectroscopy. After 12 hours, the carbodiimide band at about 2120 $cm^{-1}$ had disappeared completely. This gave a colorless, low-odor oil.

$^1$H NMR ($CDCl_3$): δ0.6-0.7 (m, 2H, $CH_2Si$), 1.05-1.45 (m, 19H), 1.55-2.1 (m, 12H), 2.60 (m, 2H, $CH_2N$), 2.75 (m, 2H, $CH_2N$), 2.9 (m, 1H, $NCH^{Cy}$), 3.11 (m, 2H, $CH_2N$), 3.23 (m, 1H, $NCH^{Cy}$), 3.70-3.85 (m, 6H, $OCH_2CH_3$).

FT-IR: 3232, 2972, 2924, 2851, 1640 (C═N), 1605, 1544, 1448, 1389, 1344, 1269, 1257, 1165, 1101, 1074, 954, 889, 772, 671.

Catalyst K-5: 1-Hexyl-2,3-dicyclohexylguanidine

In a round-bottom flask, 2.05 g of n-hexylamine and 3.68 g of N, N'-dicyclo-hexylcarbodiimide were mixed and the mixture was heated to 120° C. while stirring. At regular intervals, the reaction mixture was examined by means of FT-1R spectroscopy. After 17 hours, the carbodiimide band at about 2120 $cm^{-1}$ had disappeared completely. Thereafter, the reaction mixture was freed of the volatile constituents under reduced pressure. This gave 5.20 g of a colorless, low-odor oil.

$^1$H NMR ($CDCl_3$): δ0.9 (t, 3H, $CH_3CH_2$), 1.1-1.25 (m, 6H), 1.25-1.4 (m, 10H), 1.45-1.65 (m, 4H), 1.7-1.8 (m, 4H), 1.85-1.95 (m, 4H), 2.95-3.05 (m, 2H, $CH_2N$), 3.1-3.3 (m, 2H, $NCH^{Cy}$).

FT-IR: 3305 (N—H), 2952, 2850, 1636 (C═N), 1495, 1448, 1361, 1322, 1253, 1147, 1112, 1031, 977, 888, 723.

Catalyst K-6: 1-Hexyl-2,3-diisopropylguanidine

In a round-bottom flask, 2.93 g of n-hexylamine and 2.89 g of N, N'-diisopropyl-carbodiimide were mixed and the mixture was heated to 120° C. while stirring. At regular intervals, the reaction mixture was examined by means of FT-IR spectroscopy. After 4.5 hours, the carbodiimide band at about 2120 $cm^{-1}$ had disappeared completely. Thereafter, the reaction mixture was freed of the volatile constituents under reduced pressure. This gave 4.96 g of a pale yellow, low-odor oil.

FT-IR: 3304 (N-H), 2959, 2926, 2857, 1633 (C═N), 1510, 1466, 1378, 1363, 1336, 1172, 1125, 723.

Catalyst K-7: 1-Benzyl-2,3-dicyclohexylguanidine

In a round-bottom flask, 6.43 g of benzylamine and 10.32 g of N, N'-dicyclo-hexylcarbodiimide were mixed and the mixture was heated to 120° C. while stirring. At regular intervals, the reaction mixture was examined by means of FT-IR spectroscopy. After 70 hours, the carbodiimide band at about 2120 $cm^{-1}$ had disappeared completely. Thereafter, the reaction mixture was freed of the volatile constituents under reduced pressure. This gave 15.67 g of a pale yellow, low-odor oil.

$^1$H NMR ($CDCl_3$): δ1.1-1.5 (m, 10H), 1.55-2.0 (m, 10H), 3.11 (m, 2H, $NCH^{Cy}$), 3.6 (br s, 1H, NH), 4.31 (m, 2H, $CH_2Ph$), 4.37 (br s, 1H, NH), 7.15-7.35 (m, 5H, Ph-H).

FT-IR: 3432, 3270, 3060, 3025, 2923, 2849, 1633 (C═N), 1493, 1448, 1335, 1328, 1253, 1236, 1188, 1146, 1112, 1072, 1028, 1002, 977, 888, 860, 802, 730, 696.

Catalyst K-8:
1-(2-Ethylhexyl)-2,3-dicyclohexylguanidine

In a round-bottom flask, 7.76 g of 2-ethylhexylamine and 10.32 g of N, N'-dicyclo-hexylcarbodiimide were mixed and the mixture was heated to 120° C. while stirring. At regular intervals, the reaction mixture was examined by means of FT-IR spectroscopy. After 70 hours, the carbodiimide band at about 2120 $cm^{-1}$ had disappeared completely. Thereafter, the reaction mixture was freed of the volatile constituents under reduced pressure. This gave 16.78 g of an orange-yellow, low-odor oil.

$^1H$ NMR ($CDCl_3$): δ 0.88 (m, 6H, $CH_3$), 1.06-1.2 (m, 7H), 1.2-1.4 (m, 10H), 1.4-1.5 (m, 2H), 1.55-2.0 (m, 10H), 2.86-3.0 (m, 2H, $CH_2N$), 3.0-3.2 (m, 2H, $NCH^{Cy}$).

FT-IR: 3440, 2954, 2923, 2851, 1644 (C═N), 1493, 1448, 1361, 1335, 1255, 1236, 1188, 1145, 1090, 1050, 1027, 978, 927, 888, 845, 769, 726.

Catalyst K-9: 1-(5-Hydroxy-3-oxapentyl)-2,3-dicyclohexylguanidine

In a round-bottom flask, 3.55 g of 2-(2-aminoethoxy) ethanol (Diglycolamine® Agent, from Huntsman) and 6.81 g of N,N'-dicyclohexylcarbodiimide were mixed and the mixture was heated to 120° C. while stirring. At regular intervals, the reaction mixture was examined by means of FT-1R spectroscopy. After 24 hours, the carbodiimide band at about 2120 $cm^{-1}$ had disappeared completely. Thereafter, the reaction mixture was freed of the volatile constituents under reduced pressure. This gave 10.29 g of a pale yellow, low-odor oil.

$^1H$ NMR ($CDCl_3$): δ1.05-1.3 and 1.3-1.45 (2×m, 10H, $CH_2$), 1.54-1.78 (m, 8H), 1.88-2.0 (m, 4H), 3.13 (t, 2H, $CH_2N$), 3.69 (m, 4H, $CH_2O$), 3.81 (t, 2H, $OCH_2CH_2N$).

FT-1R: 3355(O—H), 2922, 2849, 1617 (C═N), 1520, 1447, 1340, 1257, 1240, 1117, 1066, 888, 717.

Catalyst K-10: 1-(3-Aminopropyl)-2,3-dicyclohexylguanidine

In a round-bottom flask, 2.50 g of 1,3-diaminopropane and 6.89 g of N, N'-dicyclohexylcarbodiimide were mixed and the mixture was heated to 120° C. while stirring. At regular intervals, the reaction mixture was examined by means of FT-IR spectroscopy. After 1 hour, the carbodiimide band at about 2120 $cm^{-1}$ had disappeared completely. Thereafter, the reaction mixture was freed of the volatile constituents under reduced pressure. This gave 9.36 g of a pale yellow, low-odor oil.

$^1H$ NMR ($CDCl_3$): δ1.05-1.2 and 1.25-1.40 (2×m, 10H), 1.54-1.78 (m, 10H), 1.88-2.0 (m, 4H), 2.73 (m, 2H), 3.12 (m, 2H), 3.22 (br s, 2H).

FT-IR: 3371 (N—H), 2921, 2849, 1627 (C═N), 1502, 1447, 1324, 1238, 1147, 1111, 888, 713.

Catalyst K-11: 1-(3-Cyclohexylaminopropyl)-2,3-dicyclohexylguanidine

In a round-bottom flask, 25.78 g of 3-(cyclohexylamino) propylamine (from BASF) and 30.95 g of N,N'-dicyclohexylcarbodiimide were mixed and the mixture was heated to 120° C. while stirring. At regular intervals, the reaction mixture was examined by means of FT-IR spectroscopy. After 48 hours, the carbodiimide band at about 2120 $cm^{-1}$ had disappeared completely. Thereafter, the reaction mixture was freed of the volatile constituents under reduced pressure. This gave 54.4 g of a pale yellow, low-odor oil.

FT-IR: 3283 (N—H), 2921, 2849, 1634 (C═N), 1493, 1447, 1343, 1322, 1256, 1145, 1111, 888, 713.

Catalyst K-12: 1-(3-Cyclohexylaminopropyl)-2,3-diisopropylguanidine

In a round-bottom flask, 34.38 g of 3-(cyclohexylamino) propylamine (from BASF) and 25.24 g of N,N'-diisopropylcarbodiimide were mixed and the mixture was heated to 120° C. while stirring. At regular intervals, the reaction mixture was examined by means of FT-1R spectroscopy. After 2 hours, the carbodiimide band at about 2120 $cm^{-1}$ had disappeared completely. Thereafter, the reaction mixture was freed of the volatile constituents under reduced pressure. This gave 56.50 g of a pale yellow, low-odor oil.

FT-IR: 3292 (N—H), 2960, 2924, 2852, 1633 (C═N), 1505, 1448, 1361, 1329, 1176, 1125, 889, 714.

Catalyst K-13: 1-(6-Amino-2,2(4),4-trimethylhexyl)-2,3-dicyclohexylguanidine and 1-(6-amino-3,3(5),5-trimethylhexyl)-2,3-dicyclohexylguanidine In a round-bottom flask, 16.62 g of Vestamin® TMD (mixture of 2,2,4- and 2,4,4-trimethyl-1,6-hexamethylenediamine, from Evonik) and 20.63 g of N,N'-dicyclohexylcarbodiimide were mixed and the mixture was heated to 120° C. while stirring. At regular intervals, the reaction mixture was examined by means of FT-IR spectroscopy. After 3 hours, the carbodiimide band at about 2120 $cm^{-1}$ had disappeared completely. Thereafter, the reaction mixture was freed of the volatile constituents under reduced pressure. This gave 36.5 g of a pale yellow, low-odor oil.

FT-IR: 3281 (N—H), 2923, 2850, 1635 (C═N), 1496, 1463, 1448, 1362, 1325, 1284, 1237, 1188, 1146, 1112, 1090, 1071, 1051, 1027, 977, 888, 860, 845, 804, 785, 714.

Catalyst K-14: 1-(5-Amino-2-methylpentyl)-2, 3-dicyclohexylguanidine and 1-(5-amino-4-methylpentyl)-2,3-dicyclohexylguanidine In a round-bottom flask, 12.20 g of 2-methylpentane-1, 5-diamine (MPMD; from Invista) and 20.63 g of N,N'-dicyclohexylcarbodiimide were mixed and the mixture was heated to 120° C. while stirring. At regular intervals, the reaction mixture was examined by means of FT-1R spectroscopy. After 3 hours, the carbodiimide band at about 2120 $cm^{-1}$ had disappeared completely. Thereafter, the reaction mixture was freed of the volatile constituents under reduced pressure. This gave 32.3 g of a pale yellow, low-odor oil.

FT-IR: 3304 (N—H), 2922, 2849, 1636 (C═N), 1495, 1462, 1447, 1361, 1324, 1285, 1237, 1188, 1145, 1112, 1071, 1051, 1027, 977, 926, 888, 859, 845, 802, 786, 715.

Catalyst K-15: 1-(3-(N,N-Dimethylamino)propyl)-2,3-dicyclohexylguanidine

In a round-bottom flask, 6.64 g of 3-(N,N'-dimethylamino)propylamine and 10.32 g of N,N'-dicyclohexylcarbodiimide were mixed and the mixture was heated to 120° C. while stirring. At regular intervals, the reaction mixture was examined by means of FT-IR spectroscopy. After 48 hours, the carbodiimide band at about 2120 $cm^{-1}$ had disappeared completely. Thereafter, the reaction mixture was freed of the volatile constituents under reduced pressure. This gave 15.43 g of an orange-yellow, low-odor oil.

$^1H$ NMR ($CDCl_3$): δ1.05-1.38 (m, 10H), 1.54-1.65 (m, 2H), 1.65-1.80 (m, 6H), 1.80-2.0 (m, 4H), 2.0 (s, 6H, $NMe_2$), 2.30 (m, 2H, $CH_2NMe_2$), 3.06-3.25 (m, 4H).

FT-1R: 3291, 2922, 2850, 2814, 1635 (C═N), 1494, 1447, 1361, 1322, 1256, 1236, 1147, 1098, 1068, 1040, 996, 977, 888, 845, 785, 713.

Catalyst K-16: 1-(ω-Methoxy-polyoxypropylene-polyoxyethylene)-2, 3-dicyclohexylguanidine having a molecular weight of about 810 g/mol In a round-bottom flask, 14.32 g of polyoxypropylenemonoamine having a mean molecular weight of about 600 g/mol (Jeffamine® M-600 from Huntsman, amine content about 1.7 meq/g) and 4.14 g of N,N'-dicyclohexylcarbodiimide were mixed and the mixture was heated to 120° C. while stirring. At regular intervals, the reaction mixture was examined by means of FT-IR spectroscopy. After 72 hours, the carbodiimide band at about 2120 $cm^{-1}$ had disappeared completely. This gave 18.45 g of a pale yellow, colorless oil.

FT-IR: 3367 (N—H), 2969, 2926, 2854, 1640 (C═N), 1449, 1372, 1342, 1297, 1255, 1100, 1014, 925, 889, 861, 715.

Catalyst K-17: 1,2,3-Tricyclohexylguanidine

In a round-bottom flask, 7.99 g of cyclohexylamine and 15.83 g of N, N'-dicyclohexylcarbodiimide were mixed and the mixture was heated to 120° C. while stirring. At regular intervals, the reaction mixture was examined by means of FT-IR spectroscopy. After 48 hours, the carbodiimide band at about 2120 $cm^{-1}$ had disappeared completely. Thereafter, the reaction mixture was freed of the volatile constituents under reduced pressure. This gave 23.44 g of a low-odor brown solid.

$^1H$ NMR ($CDCl_3$): δ1.05-1.38 (m, 16H), 1.54-1.65 (m, 4H), 1.65-1.80 (m, 6H), 1.8-2.0 (m, 6H), 3.06-3.25 (br s, 3H).

FT-1R: 2923, 2851, 1643 (C═N), 1491,1448, 1363, 1335, 1322, 1281, 1254, 1234, 1145, 1111, 978, 927, 846, 749, 720, 668.

Catalyst K-18: 1-(3-(3-(N,N-Dimethylamino)propyl)aminopropyl)-2, 3-dicyclohexylguanidine In a round-bottom flask, 9.40 g of $N^1$-((3-dimethylamino) propyl)-1, 3-diaminopropane and 11.65 g of N,N'-dicyclohexylcarbodiimide were mixed and the mixture was heated to 120° C. while stirring. At regular intervals, the reaction mixture was examined by means of FT-IR spectroscopy. After 3 hours, the carbodiimide band at about 2120 $cm^{-1}$ had disappeared completely. This gave a yellow, low-odor oil.

$^1H$ NMR ($CDCl_3$): δ1.05-1.38 (m, 10H), 1.54-1.70 (m, 10H), 1.80-2.0 (m, 4H), 2.21 (s, 6H, $NMe_2$), 2.30 (m, 2H, $CH_2NMe_2$), 2.58-2.70 (m, 4H, $CH_2NH$), 3.06-3.25 (m, 4H).

FT-IR: 3270, 2922, 2850, 2813, 2784, 2763, 1633 (C═N), 1495, 1447, 1359, 1335, 1321, 1257, 1237, 1097, 1041, 977, 888, 842, 785, 719.

Catalyst Ref-1: 1-Hexyl-2,3-bis(2,6-diisopropylphenyl)guanidine

In a round-bottom flask, 1.20 g of n-hexylamine and 4.01 g of bis(2, 6-diisopropylphenyl)carbodiimide (Stabilisator 7000 from Raschig) were mixed and the mixture was heated to 120° C. while stirring. At regular intervals, the reaction mixture was examined by means of FT-IR spectroscopy. After 2 hours, the carbodiimide band at about 2120 $cm^{-1}$ had disappeared completely. This gave a yellow, low-odor oil.

FT-1R: 3442, 3397, 2957, 2925, 2866, 1637 (C═N), 1585, 1513, 1459, 1434, 1391, 1361, 1324, 1300, 1255, 1198, 1179, 1126, 1098, 1058, 1044, 956, 934, 895, 831, 804, 764, 699.

Catalyst Ref-2: 1-Phenyl-2,3-diisopropylguanidine

In a test tube, 2.24 g of aniline and 2.52 g of N,N'-diisopropylcarbodiimide (DIC) were mixed and the mixture was reacted in a microwave at a temperature of 220° C. and a pressure of 150 Pa for 10 minutes. The product obtained was recrystallized from a mixture of ethyl acetate and heptane in a ratio of 1:1. This gave 2.77 g of a white solid.

$^1H$ NMR ($CDCl_3$): δ 1.08 (d, 24H, $CH_3$), 3.65 (m, 2H, CH aliph.), 6.75-6.80 (m, 2H, CH arom.), 6.82-6.88 (m, 1H, CH arom.), 7.14-7.20 (m, 2H, CH arom.).

FT-1R: 3346, 3055, 2966, 2930, 2869, 1705, 1630 (C═N), 1587, 1532, 1500, 1487, 1464, 1455, 1444, 1383, 1364, 1313, 1225, 1174, 1124, 1069, 1030, 996, 941, 898, 864, 831, 810, 755, 698.

Preparation of Polyethers Containing Silane Groups

Polymer STP-1

With exclusion of moisture, 1000 g of Acclaim® 12200 polyol (polyoxy-propylenediol having a low level of unsaturation, from Bayer; OH number 11.0 mg KOH/g), 43.6 g of isophorone diisocyanate (IPDI; Vestanat® IPDI, from Evonik), 126.4 g of diisodecyl phthalate (DIDP) and 0.1 g of bismuth tris(neodecanoate) (10% by weight in DIDP) were heated up to 90° C. while stirring constantly and left at this temperature until the content of free isocyanate groups determined by titrimetry had reached a stable value of 0.63% by weight. Subsequently, 63.0 g of diethyl N-(3-trimethoxysilylpropyl)-aminosuccinate (adduct formed from 3-aminopropyltrimethoxysilane and diethyl maleate; prepared according to the details in U.S. Pat. No. 5,364,955) were mixed in and the mixture was stirred at 90° C. until it was no longer possible to detect any free isocyanate by means of FT-IR spectroscopy. The polyether containing trimethoxysilane groups thus obtained, having a silane equivalent weight of about 6880 g/eq (calculated from the amounts used), was cooled down to room temperature and stored with exclusion of moisture.

Polymer STP-2

With exclusion of moisture, 1000 g of Acclaim ° 12200 polyol (polyoxy-propylenediol having a low level of unsaturation, from Bayer; OH number 11.0 mg KOH/g), 43.6 g of isophorone diisocyanate (IPDI; Vestanat® IPDI, from Evonik), 126.4 g of diisodecyl phthalate (DIDP) and 0.1 g of bismuth tris(neodecanoate) (10% by weight in DIDP) were heated up to 90° C. while stirring constantly and left at this temperature until the content of free isocyanate groups determined by titrimetry had reached a stable value of 0.64% by weight. Subsequently, 70.6 g of diethyl N-(3-triethoxysilylpropyl)-aminosuccinate (adduct formed from 3-aminopropyltriethoxysilane and diethyl maleate) were mixed in and the mixture was stirred at 90° C. until it was no longer possible to detect any free isocyanate by means of FT-IR spectroscopy. The polyether containing triethoxysilane groups thus obtained, having a silane equivalent weight of about 6920 g/eq (calculated from the amounts used), was cooled down to room temperature and stored with exclusion of moisture.

Commercial Catalysts Used and Abbreviations Therefor

DBU 1,8-Diazabicyclo[5.4.0]undec-7-ene
TMG 1,1,3,3-Tetramethylguanidine
DHA N,N'-Di-n-hexylacetamidine
IBAY Tyzor® IBAY, bis(ethylacetoacetato)diisobutoxytitanium(IV), from Dorf Ketal
MTHP 2-Methyl-1,4,5,6-tetrahydropyrimidine
TMTHP 2,5,5-Trimethyl-1,4,5,6-tetrahydropyrimidine
DBTDL Dibutyltin(IV) dilaurate Compositions Based on Polymers Containing Silane Groups Comparative examples are identified by (Ref) in tables 1 to 10.

Compositions B1 to B22 and Comparisons B23 to B31

A composition composed of 96.5 g of polymer STP-1, 0.5 g of vinyltrimethoxy-silane and 3.0 g of 3-aminopropyltrimethoxysilane was mixed with various catalysts in the amounts specified according to table 1, and the mixture was tested for viscosity and skin time (ST) under standard climatic conditions, before and after storage. The skin time serves as a measure of the activity of the catalyst in relation to the crosslinking reaction of the silane groups, i.e. of the crosslinking rate; the change in viscosity and the skin time after storage are a measure of storage stability. In addition, the mixture applied, after 24 hours under standard climatic conditions, was tested as to whether the surface was dry as desired or whether a greasy film had formed, which is a sign of the exudation of the catalyst owing to pure compatibility with the cured polymer, and/or whether the surface was tacky, which is a sign of incomplete curing. In addition, the mixture was used to produce a film of thickness 2 mm, which was left to cure under standard climatic conditions for 7 days and tested for mechanical properties. The results are shown in tables 1 and 2. "Comp." stands for "composition".

TABLE 1

| | | | | Viscosity [Pa · s] | | | ST | |
|---|---|---|---|---|---|---|---|---|
| Comp. | Catalyst | Amount | Concentration[1] | freshly | stored[2] | increase | freshly | stored[2] |
| B1 | K-1 | 0.41 g | 1.0 | 19.8 | 23.6 | 19% | 21' | 25' |
| B2 | K-2 | 0.37 g | 1.0 | 20.2 | 22.3 | 10% | 24' | 28' |
| B3 | K-1<br>IBAY | 0.21 g<br>0.22 g | 0.5<br>0.5 | 23.6 | 28.0 | 19% | 9' | 27' |
| B4 | K-2<br>IBAY | 0.19 g<br>0.22 g | 0.5<br>0.5 | 24.4 | 30.5 | 25% | 12' | 18' |
| B5 | K-3 | 0.80 g | 1.9 | 27.2 | 32.4 | 19% | 27' | 33' |
| B6 | K-4 | 0.87 g | 1.9 | 26.8 | 34.1 | 27% | 30' | 32' |
| B7 | K-5 | 0.56 g | 1.9 | 37.6 | 37.7 | 0.3% | 12' | 13' |
| B8 | K-5<br>IBAY | 0.15 g<br>0.22 g | 0.5<br>0.5 | 48.0 | 50.6 | 5% | 20' | 25' |
| B9 | K-6 | 0.42 g | 1.9 | 24.1 | 27.0 | 12% | 15' | 18' |
| B10 | K-7 | 0.58 g | 1.9 | 27.8 | 30.0 | 8% | 20' | 19' |
| B11 | K-8 | 0.62 g | 1.9 | 26.2 | 29.4 | 12% | 16' | 17' |
| B12 | K-9 | 0.57 g | 1.9 | 26.1 | 31.5 | 21% | 13' | 16' |
| B13 | K-9<br>IBAY | 0.15 g<br>0.22 g | 0.5<br>0.5 | 35.0 | 39.4 | 11.2% | 21' | 28' |
| B14 | K-10 | 0.51 g | 1.9 | 21.4 | 28.4 | 33% | 12' | 13' |
| B15 | K-11 | 0.66 g | 1.9 | 24.1 | 27.3 | 13% | 5' | 13' |
| B16 | K-12 | 0.52 g | 1.9 | 22.8 | 28.0 | 23% | 9' | 13' |
| B17 | K-13 | 0.67 g | 1.9 | 28.4 | 39.9 | 41% | 11' | 7' |
| B18 | K-14 | 0.59 g | 1.9 | 27.7 | 40.1 | 45% | 14' | 8' |
| B19 | K-15 | 0.56 g | 1.9 | 24.3 | 25.7 | 6% | 6' | 7' |
| B20 | K-15<br>IBAY | 0.15 g<br>0.22 g | 0.5<br>0.5 | 50.9 | 52.0 | 2% | 12' | 17' |
| B21 | K-17[3] | 0.57 g | 1.9 | 26.0 | 27.2 | 4% | 13' | 14' |
| B22 | K-18 | 0.67 g | 1.9 | 21.8 | 26.9 | 23% | 8' | 12' |
| B23 (Ref) | DBU | 0.28 g | 1.9 | 27.2 | 36.9 | 36% | 25' | 29' |
| B24 (Ref) | TMG | 0.21 g | 1.9 | 22.3 | 24.6 | 10% | 65' | 75' |
| B25 (Ref) | DHA | 0.42 g | 1.9 | 24.8 | 32.6 | 31% | 40' | 48' |
| B26 (Ref) | IBAY | 0.87 g | 2.0 | 24.8 | 30.2 | 22% | 45' | 2 h |
| B27 (Ref) | DBU<br>IBAY | 0.07 g<br>0.22 g | 0.5<br>0.5 | 24.9 | 28.1 | 13% | 15' | 55' |
| B28 (Ref) | TMG<br>IBAY | 0.06 g<br>0.22 g | 0.5<br>0.5 | 23.2 | 25.0 | 8% | 37' | 111' |
| B29 (Ref) | — | — | — | 24.8 | 28.9 | 17% | 87' | 110' |
| B30 (Ref) | Ref-1 | 0.85 g | 1.9 | 22.3 | 22.4 | 0% | 95' | 100' |
| B31 (Ref) | Ref-2[3] | 0.40 g | 1.9 | 20.5 | 21.8 | 6% | 108' | 107' |

[1]mmol of amidine or guanidine groups or metal atoms per 100 g of polyether containing silane groups.

[2]for 7 days at 60° C. in a closed container.

[3]as a solution (20% by weight) in N-ethylpyrrolidone.

TABLE 2

| Comp. | Surface after 24 h | Tensile strength | Elongation at break | Modulus of elasticity 0-5% | Modulus of elasticity 0-50% |
|---|---|---|---|---|---|
| B1 | dry | 0.59 MPa | 77% | 1.18 MPa | 0.77 MPa |
| B2 | dry | 0.57 MPa | 72% | 1.17 MPa | 0.78 MPa |
| B3 | dry | 0.63 MPa | 90% | 1.13 MPa | 0.75 MPa |
| B4 | dry | 0.54 MPa | 69% | 1.17 MPa | 0.76 MPa |
| B5 | dry | 0.78 MPa | 116% | 1.11 MPa | 0.80 MPa |
| B6 | dry | 0.73 MPa | 98% | 1.08 MPa | 0.81 MPa |
| B7 | dry | 0.60 MPa | 76% | 1.18 MPa | 0.81 MPa |
| B8 | dry | 0.59 MPa | 73% | 1.26 MPa | 0.81 MPa |
| B9 | dry | 0.57 MPa | 75% | 1.14 MPa | 0.76 MPa |
| B10 | dry | 0.74 MPa | 114% | 0.98 MPa | 0.76 MPa |
| B11 | dry | 0.69 MPa | 105% | 1.08 MPa | 0.76 MPa |
| B12 | dry | 0.61 MPa | 78% | 1.05 MPa | 0.75 MPa |
| B13 | dry | 0.68 MPa | 95% | 1.17 MPa | 0.80 MPa |
| B14 | dry | 0.70 MPa | 98% | 1.04 MPa | 0.78 MPa |
| B15 | dry | 0.69 MPa | 97% | 1.07 MPa | 0.78 MPa |
| B16 | dry | 0.70 MPa | 95% | 1.04 MPa | 0.79 MPa |
| B17 | dry | 0.72 MPa | 102% | 1.23 MPa | 0.79 MPa |
| B18 | dry | 0.70 MPa | 91% | 1.20 MPa | 0.81 MPa |
| B19 | dry | 0.73 MPa | 105% | 1.11 MPa | 0.78 MPa |
| B20 | dry | 0.65 MPa | 87% | 1.24 MPa | 0.81 MPa |
| B21 | dry | 0.59 MPa | 73% | 1.19 MPa | 0.81 MPa |
| B22 | dry | 0.63 MPa | 84% | 1.23 MPa | 0.81 MPa |
| B23 (Ref) | greasy | 0.58 MPa | 72% | 1.16 MPa | 0.77 MPa |

TABLE 2-continued

| Comp. | Surface after 24 h | Tensile strength | Elongation at break | Modulus of elasticity 0-5% | Modulus of elasticity 0-50% |
|---|---|---|---|---|---|
| B24 (Ref) | tacky | 0.62 MPa | 90% | 1.19 MPa | 0.75 MPa |
| B25 (Ref) | slightly tacky | 0.63 MPa | 82% | 1.10 MPa | 0.78 MPa |
| B26 (Ref) | tacky | 0.59 MPa | 91% | 1.05 MPa | 0.69 MPa |
| B27 (Ref) | slightly greasy | 0.60 MPa | 81% | 1.11 MPa | 0.76 MPa |
| B28 (Ref) | slightly tacky | 0.69 MPa | 100% | 1.13 MPa | 0.76 MPa |
| B29 (Ref) | dry | 0.68 MPa | 112% | 1.02 MPa | 0.69 MPa |
| B30 (Ref) | dry | 0.59 MPa | 79% | 1.17 MPa | 0.74 MPa |
| B31 (Ref) | dry | 0.76 MPa | 117% | 0.79 MPa | 0.75 MPa |

Compositions B32 to B49 and Comparisons B50 to B56

A composition composed of 95.9 g of polymer STP-2, 0.4 g of vinyltriethoxy-silane and 3.7 g of N-(2-aminoethyl)-3-aminopropyltriethoxysilane was blended with various catalysts in the amounts specified according to table 3 and the mixture was tested as described for composition B1 for viscosity, skin time (ST), surface characteristics and mechanical properties. The results are shown in tables 3 and 4. "Comp." stands for "composition".

TABLE 3

| Comp. | Catalyst | Amount | Concentration[1] | Viscosity [Pa · s] freshly | Viscosity [Pa · s] stored[2] | Viscosity [Pa · s] increase | ST freshly | ST stored[2] |
|---|---|---|---|---|---|---|---|---|
| B32 | K-1 | 1.56 g | 3.8 | 46.2 | 50.4 | 9% | 50' | 50' |
| B33 | K-2 | 1.41 g | 3.8 | 48.0 | 53.8 | 12% | 55' | 39' |
| B34 | K-1 | 0.62 g | 1.5 | 40.3 | 48.0 | 19% | 72' | 70' |
| | IBAY | 0.82 g | 1.9 | | | | | |
| B35 | K-2 | 0.55 g | 1.5 | 39.5 | 48.9 | 24% | 70' | 50' |
| | IBAY | 0.82 g | 1.9 | | | | | |
| B36 | K-3 | 1.56 g | 3.8 | 30.4 | 33.6 | 10% | 5 h 30' | 2 h 12' |
| B37 | K-4 | 1.72 g | 3.8 | 31.5 | 34.6 | 10% | 2 h 7' | 4 h 56' |
| B38 | K-5 | 1.15 g | 3.8 | 35.1 | 38.5 | 10% | 60' | 80' |
| B39 | K-5 | 0.58 g | 1.9 | 50.1 | 54.5 | 9% | 100' | 85' |
| | IBAY | 0.79 g | 1.6 | | | | | |
| B40 | K-6 | 0.83 g | 3.8 | 33.8 | 37.3 | 10% | 65' | 60' |
| B41 | K-8 | 1.22 g | 3.8 | 33.6 | 35.4 | 5% | 128' | 100' |
| B42 | K-9 | 1.14 g | 3.8 | 34.6 | 35.7 | 3% | 90' | 70' |
| 643 | K-9 | 0.58 g | 1.9 | 49.8 | 59.9 | 20% | 95' | 44' |
| | IBAY | 0.79 g | 1.6 | | | | | |
| B44 | K-13 | 1.33 g | 3.8 | 33.9 | 42.7 | 26% | 92' | 40' |
| B45 | K-14 | 1.18 g | 3.8 | 33.3 | 41.3 | 24% | 81' | 35' |
| B46 | K-15 | 1.12 g | 3.8 | 34.5 | 37.2 | 8% | 56' | 36' |
| B47 | K-15 | 0.58 g | 1.9 | 51.2 | 59.0 | 15% | 50' | 50' |
| | IBAY | 0.79 g | 1.6 | | | | | |
| B48 | K-16 | 2.94 g | 3.8 | 32.9 | 35.4 | 8% | 75' | 75' |
| B49 | K-17[3] | 1.14 g | 3.8 | 31.3 | 33.9 | 8% | 77' | 66' |
| B50 (Ref) | DBU | 0.55 g | 3.8 | 48.8 | 58.1 | 19% | 127' | 155' |
| B51 (Ref) | TMG | 0.42 g | 3.8 | 44.5 | 53.4 | 20% | >12 h | >12 h |
| B52 (Ref) | DHA | 0.83 g | 3.8 | 35.5 | 55.4 | 56% | 5 h 30' | 4 h 15' |
| B53 (Ref) | MTHP | 0.36 g | 3.8 | 46.5 | 54.0 | 16% | 120' | 110' |
| B54 (Ref) | TMTHP[3] | 0.36 g | 3.0 | 30.0 | 34.4 | 15% | 3 h 40' | 3 h |
| B55 (Ref) | DBU | 0.22 g | 1.5 | 43.2 | 45.6 | 6% | 3 h 20' | 3 h |
| | IBAY | 0.82 g | 1.9 | | | | | |
| B56 (Ref) | TMG | 0.17 g | 1.5 | 38.2 | 42.8 | 12% | >24 h | >24 h |
| | IBAY | 0.82 g | 1.9 | | | | | |

[1]mmol of amidine or guanidine groups or metal atoms per 100 g of polyether containing silane groups.

[2]for 7 days at 60° C. in a closed container.

[3]as a solution (20.0% by weight) in N-ethylpyrrolidone.

TABLE 4

| Comp. | Surface after 24 h | Tensile strength | Elongation at break | Modulus of elasticity 0-5% | 0-50% |
|---|---|---|---|---|---|
| B32 | almost dry | 0.64 MPa | 170% | 0.72 MPa | 0.48 MPa |
| B33 | almost dry | 0.66 MPa | 176% | 0.69 MPa | 0.48 MPa |
| B34 | almost dry | 0.58 MPa | 138% | 0.70 MPa | 0.48 MPa |
| B35 | almost dry | 0.59 MPa | 140% | 0.68 MPa | 0.49 MPa |
| B36 | dry | 0.62 MPa | 147% | 0.40 MPa | 0.49 MPa |
| B37 | dry | 0.62 MPa | 125% | 0.64 MPa | 0.57 MPa |
| B38 | dry | 0.54 MPa | 97% | 0.86 MPa | 0.59 MPa |
| B39 | dry | 0.62 MPa | 112% | 0.95 MPa | 0.65 MPa |
| B40 | dry | 0.66 MPa | 125% | 0.87 MPa | 0.62 MPa |
| B41 | dry | 0.60 MPa | 111% | 0.60 MPa | 0.58 MPa |
| B42 | dry | 0.63 MPa | 115% | 0.85 MPa | 0.61 MPa |
| B43 | slightly tacky | 0.68 MPa | 142% | 0.76 MPa | 0.60 MPa |
| B44 | dry | 0.63 MPa | 115% | 1.02 MPa | 0.65 MPa |
| B45 | dry | 0.58 MPa | 96% | 0.95 MPa | 0.65 MPa |
| B46 | dry | 0.62 MPa | 117% | 0.75 MPa | 0.60 MPa |
| B47 | dry | 0.65 MPa | 121% | 0.93 MPa | 0.64 MPa |
| B48 | dry | 0.63 MPa | 141% | 0.77 MPa | 0.55 MPa |
| B49 | dry | 0.61 MPa | 112% | 0.97 MPa | 0.65 MPa |
| B50 (Ref) | greasy, tacky | 0.55 MPa | 152% | 0.48 MPa | 0.44 MPa |
| B51 (Ref) | very severely tacky | n.d. | n.d. | n.d. | n.d. |
| B52 (Ref) | severely tacky | 0.55 MPa | 99% | 0.92 MPa | 0.57 MPa |
| B53 (Ref) | greasy, tacky | 0.53 MPa | 165% | 0.52 MPa | 0.39 MPa |
| B54 (Ref) | greasy, tacky | 0.45 MPa | 80% | 0.71 MPa | 0.54 MPa |

TABLE 4-continued

| Comp. | Surface after 24 h | Tensile strength | Elongation at break | Modulus of elasticity 0-5% | 0-50% |
|---|---|---|---|---|---|
| B55 (Ref) | slightly greasy and tacky | 0.66 MPa | 145% | 0.81 MPa | 0.56 MPa |
| B56 (Ref) | (liquid) | n.d. | n.d. | n.d. | n.d. |

n.d. = not determined or not measurable.

Compositions B57 to B61 and Comparison B62

In a planetary mixer, 36.2 g of polymer STP-1, 60.2 g of ground chalk (Omyacarb® 5 GU, from Omya), 1.2 g of thixotropic paste prepared as described below, 1.2 g of vinyltrimethoxysilane, 1.2 g of 3-aminopropyl-trimethoxysilane and various catalysts in the amounts specified according to table 5 were blended and the mixture was tested as described for composition B1 for viscosity, skin time (ST), surface characteristics and mechanical properties. The results are shown in table 5. "Comp." stands for "composition". The thixotropic paste was prepared by initially charging a vacuum mixer with 300 g of diisodecyl phthalate (Palatinol® Z, from BASF) and 48 g of 4, 4'-methylenediphenyl diisocyanate (Desmodur® 44 MC L, from Bayer), gently heating the contents and then gradually adding 27 g of n-butylamine dropwise while stirring vigorously. The resultant paste was stirred under reduced pressure and with cooling for a further hour.

TABLE 5

| Comp. | Catalyst | Amount | Concentration[1] | ST | Surface after 24 h | Tensile strength | Elongation at break | Modulus of elasticity [MPa] 0-5% | 0-100% |
|---|---|---|---|---|---|---|---|---|---|
| B57 | K-2 | 0.31 g | 0.8 | 11' | dry | 3.1 MPa | 117% | 6.2 | 3.0 |
| B58 | K-6 | 0.18 g | 0.8 | 9' | dry | 2.8 MPa | 136% | 6.1 | 2.5 |
| B59 | K-13 | 0.29 g | 0.8 | 20' | dry | 2.7 MPa | 110% | 6.3 | 2.5 |
| B60 | K-14 | 0.26 g | 0.8 | 19' | dry | 2.8 MPa | 120% | 6.0 | 2.6 |
| B61 | K-15 | 0.25 g | 0.8 | 9' | dry | 2.5 MPa | 111% | 6.2 | 3.7 |
| B62 (Ref) | DBU | 0.12 g | 0.8 | 25' | slightly greasy | 2.5 MPa | 103% | 6.1 | 2.8 |

1mmol of amidine or guanidine groups per 100 g of composition.

Compositions B63 to B67 and Comparisons B68 and B69

In a planetary mixer, 36.2 g of polymer STP-2, 60.2 g of ground chalk (Omyacarb® 5 GU, from Omya), 1.2 g of thixotropic paste prepared as described for composition Z27, 1.2 g of vinyltriethoxysilane, 1.2 g of 3-minopropyltriethoxysilane and various catalysts in the amounts specified according to table 6 were blended and the mixture was tested as described for composition B1 for skin time (ST), surface characteristics and mechanical properties. The results are shown in table 6. "Comp." stands for "composition".

TABLE 6

| Comp. | Catalyst | Amount | Concentration[1] | ST | Surface after 24 h | Tensile strength | Elongation at break | Modulus of elasticity [MPa] 0-5% | 0-100% |
|---|---|---|---|---|---|---|---|---|---|
| B63 | K-1 | 1.11 g | 2.6 | 48' | dry | 3.5 MPa | 124% | 5.7 | 3.1 |
| B64 | K-1<br>IBAY | 0.55 g<br>0.59 g | 1.3<br>1.3 | 50' | dry | 2.3 MPa | 165% | 4.7 | 2.0 |

TABLE 6-continued

| Comp. | Catalyst | Amount | Concentration[1] | ST | Surface after 24 h | Tensile strength | Elongation at break | Modulus of elasticity [MPa] 0-5% | 0-100% |
|---|---|---|---|---|---|---|---|---|---|
| B65 | K-5 | 0.80 g | 2.6 | 51' | dry | 2.7 MPa | 145% | 5.0 | 2.3 |
| B66 | K-6 | 0.59 g | 2.6 | 52' | dry | 2.8 MPa | 139% | 5.0 | 2.4 |
| B67 | K-15 | 0.80 g | 2.6 | 30' | dry | 2.5 MPa | 158% | 4.3 | 2.5 |
| B68 (Ref) | DBU | 0.40 g | 2.6 | 83' | greasy | 2.5 MPa | 155% | 4.0 | 2.0 |
| B69 (Ref) | DBU<br>IBAY | 0.20 g<br>0.59 g | 1.3<br>1.3 | 63' | slightly greasy | 2.2 MPa | 184% | 3.6 | 1.8 |

[1]mmol of amidine or guanidine groups or metal atoms per 100 g of polyether containing silane groups.

Composition B70 (In Situ Preparation of the Catalyst)

A composition composed of 20.0 g of polymer STP-1 and 0.6 g of 3-amino-propyltrimethoxysilane, with exclusion of moisture, was blended with 0.95 g of a solution of N,N'-dicyclohexylcarbodiimide (49.8% by weight in N-ethyl-pyrrolidone), and the mixture was dispensed into an internally coated aluminum tube and heated to 80° C. in an oven. After the time intervals specified in table 7, the mixture was tested for skin time (ST) under standard climatic conditions and for the conversion of the carbodiimide (via decrease in the intensity of the carbodiimide band at about 2120 $cm^{-1}$ in the FT-IR, intensity at the start=0% conversion, no band detectable any longer=100% conversion). The results are shown in table 7.

TABLE 7

| Time | ST | Carbodiimide conversion |
|---|---|---|
| 0 h | 115' | 0% |
| 1 h | 70' | 3% |
| 2 h | 40' | 14% |
| 4 h | 17' | 36% |
| 5 h | 13' | 48% |
| 23 h | 7' | 92% |

Compositions B71 to B76 and Comparisons B77 to B79

A composition composed of 98 g of MS Polymer™ S203H, a polyether containing silane groups (from Kaneka), and 2 g of 3-aminopropyltrimethoxy-silane was blended with various catalysts in the amounts specified according to table 8 and the mixture was tested as described for skin time (ST) and surface characteristics after 7 days under standard climatic conditions. The results are shown in table 8. “Comp.” stands for “composition”.

TABLE 8

| Comp. | Catalyst | Amount | Concentration[1] | ST | Surface after 7 d |
|---|---|---|---|---|---|
| B71 | K-1 | 10.26 g | 24.0 | 3 h | almost dry |
| B72 | DBTDL | 1.52 g | 2.4 | 50' | dry |
| | K-1 | 1.71 g | 4.0 | | |
| B73 | K-5 | 7.40 g | 24.0 | 4 h 15' | almost dry |
| B74 | DBTDL | 0.76 g | 1.2 | 63' | dry |
| | K-5 | 3.71 g | 12.0 | | |
| B75 | K-15 | 7.40 g | 24.0 | 2 h 25' | almost dry |
| B76 | DBTDL | 0.76 g | 1.2 | 75' | dry |
| | K-15 | 3.70 g | 12.0 | | |
| B77 (Ref) | DBU | 3.65 g | 24.0 | >12 h | greasy and tacky |
| B78 (Ref) | DBTDL | 1.52 g | 2.4 | 71' | dry |
| B79 (Ref) | DBTDL | 0.76 g | 1.2 | 85' | greasy and tacky |
| | DBU | 1.83 g | 12.0 | | |

[1]mmol of amidine or guanidine groups or metal atoms per 100 g of polyether containing silane groups.

Compositions B80 to B85 and Comparisons B86 to B89

A composition composed of 96.5 g of TEGOPAC® Bond 150, a polyether containing silane groups (from Evonik), 0.5 g of vinyltriethoxysilane and 3.0 g of 3-aminopropyltriethoxysilane was blended with various catalysts in the amounts specified according to table 9 and the mixture was tested as described for skin time (ST) and surface characteristics after 7 days under standard climatic conditions. The results are shown in table 9. “Comp.” stands for “composition”.

TABLE 9

| Comp. | Catalyst | Amount | Concentration[1] | ST | Surface after 7 d |
|---|---|---|---|---|---|
| B80 | K-1 | 6.19 g | 15 | 56' | almost dry |
| B81 | K-1 | 2.15 g | 5 | 3 h | almost dry |
| | IBAY | 2.40 g | 5 | | |
| B82 | K-5 | 4.61 g | 15 | 81' | almost dry |
| B83 | K5 | 1.54 g | 5 | 105' | dry |
| | IBAY | 2.42g | 5 | | |
| B84 | K-15 | 4.64 g | 15 | 53' | dry |
| B85 | K-15 | 1.54 g | 5 | 63' | dry |
| | IBAY | 2.42 g | 5 | | |
| B86 (Ref) | DBU | 2.28 g | 15 | 4 h 20' | greasy |
| B87 (Ref) | DBTDL | 0.79 g | 1.25 | 1 h 45' | dry |
| B88 (Ref) | IBAY | 7.25 g | 15 | 2 h | soft and tacky |
| B89 (Ref) | DBU | 4.93 g | 5 | 3 h | tacky |
| | IBAY | 2.40 g | 5 | | |

[1]mmol of amidine or guanidine groups or metal atoms per 100 g of polyether containing silane groups.

Compositions B90 to B95 and Comparisons B96 and B97

A composition composed of 96.0 g of polyether containing silane groups, either GENIOSIL® STP-E 15 (from Wacker) or Desmoseal® S XP 2821 (from Bayer), 0.35 g of vinyltrimethoxysilane and 3.72 g of 3-aminopropyltrimethoxysilane was blended with various catalysts in the amounts specified according to table 10 and the mixture was tested as described for composition B1. The results are shown in table 10. "Comp." stands for "composition".

TABLE 10

| Comp. | Polymer | Catalyst, amount | Concentration[1] | ST | Surface after 24 h | Tensile strength | Elongation at break | Modulus of elasticity 0-5% |
|---|---|---|---|---|---|---|---|---|
| B90 | E-15[2] | K-1, 0.81 g | 1.9 | 18' | dry | 0.76 MPa | 48% | 1.91 MPa |
| B91 | E-15[2] | K-5 0.58 | 1.9 | 15' | dry | 0.72 MPa | 44% | 2.04 MPa |
| B92 | E-15[2] | K-15 0.58 | 1.9 | 10' | dry | 0.85 MPa | 59% | 1.94 MPa |
| B93 | 2821[3] | K-1, 0.81 g | 1.9 | 50' | dry | 0.96 MPa | 31% | 3.3 MPa |
| B94 | 2821[3] | K-5 0.58 | 1.9 | 42' | dry | 0.82 MPa | 28% | 3.22 MPa |
| B95 | 2821[3] | K-15 0.58 | 1.9 | 32' | dry | 0.93 MPa | 33% | 3.21 MPa |
| B96 (Ref) | E-15[2] | DBU, 0.28 g | 1.9 | 60' | greasy | 0.72 MPa | 48% | 1.84 MPa |
| B97 (Ref) | 2821[3] | DBU, 0.28 g | 1.9 | 55' | dry | 0.85 MPa | 28% | 3.20 MPa |

[1]mmol of amidine or guanidine groups per 100 g of polyether containing silane groups.
[2]GENIOSIL ® STP-E 15 (from Wacker)
[3]Desmoseal ® S XP 2821 (from Bayer)

The invention claimed is:

1. A process for producing a composition comprising at least one organic polymer containing silane groups; and at least one catalyst of the formula (I),

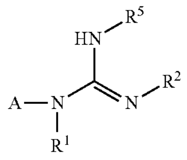

(I)

wherein

A is an aliphatic or cycloaliphatic or arylaliphatic hydrocarbyl radical which has 1 to 100 carbon atoms, optionally contains unsaturated moieties, optionally contains heteroatoms and optionally has amino groups or hydroxyl groups, or together with $R^1$ is a divalent, optionally branched alkylene radical which has 4 to 12 carbon atoms and optionally contains a heteroatom, $R^1$ is hydrogen or an alkyl or cycloalkyl or aralkyl radical having 1 to 8 carbon atoms, or together with A is a divalent, optionally branched alkylene radical which has 4 to 12 carbon atoms and optionally contains a heteroatom, and $R^2$ and $R^5$ are each independently an alkyl, cycloalkyl or aralkyl radical which has 1 to 18 carbon atoms and optionally contains heteroatoms, wherein A is a different radical from each of $R^2$ and $R^5$;

wherein the catalyst of the formula (I) does not contain any nitrogen atom bonded directly to an aromatic ring or part of a heteroaromatic ring system, and the catalyst of the formula (I) is free of silane groups, and wherein the composition is free of carbodiimide, the process comprising preparing a catalyst of the formula (I), wherein at least one amine of the formula (II) is reacted with at least one carbodiimide of the formula (III),

(II)

$R^5—N=C=N—R^2$ and (III)

adding the prepared catalyst to the at least one organic polymer containing silane groups or to a composition comprising the at least one organic polymer containing silane groups, wherein the adding is effected by preparing the catalyst in the presence of the at least one organic polymer containing silane groups.

2. The process as claimed in claim 1, wherein A is selected from the group consisting of n-hexyl, n-octyl, 2-ethylhexyl, n-decyl, lauryl, cyclohexyl, benzyl, 2-methoxyethyl, 3-methoxypropyl, polyoxyalkylene radical having oxyethylene and 1,2-oxypropylene units and a molecular weight in the range from about 180 to 600 g/mol, N-methyl-3-aminopropyl, N-(2-ethylhexyl)-3-aminopropyl, N-cyclohexyl-3-aminopropyl, 3-(N,N-dimethylamino)propyl, 2-aminopropyl, 3-aminopropyl, 3-aminopentyl, 5-amino-4-methylpentyl, 5-amino-2-methylpentyl, 6-aminohexyl, 6-amino-3,3(5),5-trimethylhexyl, 6-amino-2,2(4),4-trimethylhexyl, 8-aminooctyl, 10-aminodecyl, 12-aminododecyl, 3-aminomethyl-3,5,5-trimethylcyclohexyl, 3-amino-1,5,5-trimethylcyclo-hexylmethyl, 3-aminomethylcyclohexylmethyl, 4-aminomethylcyclohexyl-methyl, 3-aminomethylbenzyl, 5-amino-3-oxapentyl, ω-2-aminopropyl-polyoxypropylene radical having a molecular weight in the range from about 200 to 500 g/mol, 2-hydroxypropyl, 3-hydroxypropyl, 1,1-dimethyl-2-hydroxyethyl, and 5-hydroxy-3-oxapentyl.

3. The process as claimed in claim 1, wherein $R^1$ is hydrogen.

4. The process as claimed in claim 1, wherein $R^2$ and $R^5$ are each independently ethyl, isopropyl, tert-butyl, 3-(dimethylamino)propyl or cyclohexyl.

5. The process as claimed in claim 1, wherein the organic polymer containing silane groups is a polyolefin containing silane groups or a polyester containing silane groups or a poly(meth)acrylate containing silane groups or a polyether containing silane groups or a mixed form of these polymers.

6. The process as claimed in claim 1, wherein at least one organotitanate is additionally present.

7. The process as claimed in claim 1, wherein the amine of the formula (II) is selected from the group consisting of n-hexylamine, n-octylamine, 2-ethylhexylamine, n-decylamine, laurylamine, cyclohexyl-amine, benzylamine, 2-methoxyethylamine, 3-methoxypropylamine, polyoxyalkyleneamine having oxyethylene and 1,2-oxypropylene units and a mean molecular weight in the range from 180 to 600 g/mol, N-methyl-1,3-propanediamine, N-(2-ethylhexyl)-1,3-propanediamine, N-cyclohexyl-1,3-propanediamine, N,N-dimethyl-1,3-propanediamine, 1,2-propanediamine, 1,3-propanediamine, 1,3-pentanediamine, 1,5-diamino-2-methylpentane, 1,6-hexanediamine, 2,2,4- and 2,4,4-trimethylhexa-methylenediamine, 1,8-octanediamine, 1,10-decanediamine, 1,12-dodecanediamine, 1-amino-3-aminomethyl-3,5,5-trimethylcyclohexane, 1,3-bis(aminomethyl)cyclohexane, 1,4-bis(aminomethyl)cyclohexane, 1,3-bis(aminomethyl)benzene, bis(2-aminoethyl) ether, polyoxypropylene-diamine having a mean molecular weight in the range from about 220 to 500 g/mol, 1-amino-2-propanol, 3-amino-1-propanol, 2-amino-2-methyl-1-propanol, and 2-(2-aminoethoxy)ethanol.

8. The process as claimed in claim 1, wherein the carbodiimide of the formula (III) is selected from the group consisting of N,N'-diisopropylcarbodiimide, N,N'-di-tert-butylcarbodiimide, N,N'-dicyclohexylcarbodiimide and N-ethyl-N'-(3-dimethylaminopropyl)-carbodiimide.

9. A method for adhesively bonding, sealing, or coating a substrate, including the step of applying the composition produced in the process of claim 1 as an adhesive, sealant or coating to the substrate and exposing the composition to water.

10. A cured composition obtained from the composition produced in the process of claim 1 after it has been cured with water.

11. A method for catalytic crosslinking an organic polymer containing silane groups comprised in the composition produced in the process of claim 1, including exposing the composition to water.

12. A catalyst comprised of 1-(3-(N,N-dimethylamino)propyl)-2,3-dicyclohexylguanidine.

* * * * *